(12) United States Patent
Tsubouchi et al.

(10) Patent No.: US 11,643,649 B2
(45) Date of Patent: May 9, 2023

(54) CELLULAR PHENOTYPE SCREENING METHOD

(71) Applicants: ThinkCyte, Inc., Tokyo (JP); The University of Tokyo, Tokyo (JP); RIKEN, Saitama (JP)

(72) Inventors: Asako Tsubouchi, Tokyo (JP); Sadao Ota, Tokyo (JP); Fumiko Kawasaki, Wako (JP)

(73) Assignees: ThinkCyte, Inc., Tokyo (JP); The University of Tokyo, Tokyo (JP); RIKEN, Saitama (JP)

( * ) Notice: Subject to any disclaimer, the term of this patent is extended or adjusted under 35 U.S.C. 154(b) by 0 days.

(21) Appl. No.: 17/770,569

(22) PCT Filed: Jan. 12, 2021

(86) PCT No.: PCT/JP2021/000735
§ 371 (c)(1),
(2) Date: Apr. 20, 2022

(87) PCT Pub. No.: WO2021/141138
PCT Pub. Date: Jul. 15, 2021

(65) Prior Publication Data
US 2023/0058670 A1    Feb. 23, 2023

Related U.S. Application Data

(60) Provisional application No. 62/959,420, filed on Jan. 10, 2020.

(51) Int. Cl.
C40B 30/04    (2006.01)
C12N 15/10    (2006.01)

(52) U.S. Cl.
CPC ...... *C12N 15/1055* (2013.01); *C12N 15/1065* (2013.01); *C12N 15/1089* (2013.01); *C40B 30/04* (2013.01)

(58) Field of Classification Search
None
See application file for complete search history.

(56) References Cited

U.S. PATENT DOCUMENTS

2017/0166959 A1    6/2017    Hashimoto et al.
2020/0131562 A1    4/2020    Yachie et al.

FOREIGN PATENT DOCUMENTS

WO    WO2015166768 A1    11/2015
WO    WO2017073737 A1    5/2017
WO    WO2018181458 A1    10/2018
(Continued)

OTHER PUBLICATIONS

Author manuscript of McGinnis et al., *Nature Methods*, 16(7):619-626, 2019.
(Continued)

*Primary Examiner* — Christian C Boesen
(74) *Attorney, Agent, or Firm* — Lathrop GPM LLP; Brian C. Trinque

(57) ABSTRACT

The present disclosure provides a method for screening cells, the method including a step of preparing a plurality of cells which are tagged with a first barcode nucleic acid associated with a test target and treated with the test target, a step of sorting the plurality of cells based on cellular phenotype using an imaging cell sorter, and a step of identifying the test target used to treat each cell using the first barcode nucleic acid as an indicator.

20 Claims, 22 Drawing Sheets

Specification includes a Sequence Listing.

(56) References Cited

FOREIGN PATENT DOCUMENTS

| WO | WO2018203576 A1 | 11/2018 |
| WO | WO2018226293 A1 | 12/2018 |
| WO | WO2020096015 A1 | 5/2020 |

OTHER PUBLICATIONS

Hatori, et al., "Particle-Templated Emulsification for Microfluidics-Free Digital Biology", *Analytical Chemistry*, 90:9813-9820, 2018.

International Search Report for PCT Application No. PCT/JP2021/000735, dated Apr. 6, 2021, 6 pages.

Kim, et al., "Single-Cell RT-PCR in Microfluidic Droplets with Integrated Chemical Lysis, *Analytical Chemistry*", 90:1273-1279, 2018.

Japanese Office Action for JP Application No. 2021-570124, dated Feb. 15, 2022, 7 pages.

McGinnis, et al., "MULTI-seq: Universal sample multiplexing for single-cell RNA sequencing lipid-tagged indices", Nature Methods, 16(7):619-626, 2019.

Written Opinion for PCT Application No. PCT/JP2021/000735, dated Apr. 6, 2021, 12 pages.

FIG. 4

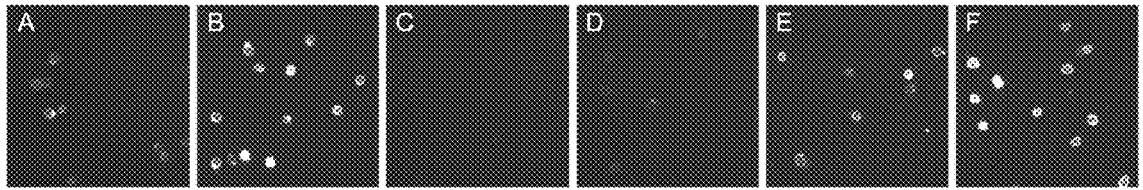

A: INCUBATION AT 4 DEGREES IN PBS SOLUTION
B: INCUBATION AT ROOM TEMPERATURE IN PBS SOLUTION
C: INCUBATION AT 4 DEGREES IN RPMI MEDIUM WITH 10% SERUM
D: INCUBATION AT ROOM TEMPERATURE IN RPMI MEDIUM WITH 10% SERUM
E: INCUBATION AT 4 DEGREES IN OPTI-MEM MEDIUM
F: INCUBATION AT ROOM TEMPERATURE IN OPTI-MEM MEDIUM

FIG. 5

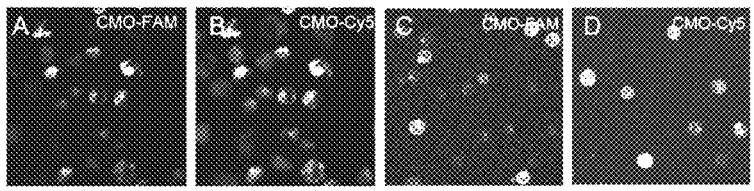

THE RESULTS OF MIXING THE CELLS TAGGED WITH BARCODE A AND THE CELLS TAGGED WITH BARCODE B IN PBS SOLUTION AND INCUBATING FOR ONE HOUR. THE BARCODES FELL OFF THE CELLS AND THE TWO TYPES OF BARCODE NUCLEIC ACIDS WERE MIXED WITH EACH OTHER.
A: VISUALIZE BARCODE A
B: VISUALIZE BARCODE B

THE RESULTS OF MIXING THE CELLS TAGGED WITH BARCODE A AND THE CELLS TAGGED WITH BARCODE B IN RPMI-1640 MEDIUM WITH 10% FBS AND 50 $\mu$M 2-MERCAPTO ETHANOL AND INCUBATING FOR ONE HOUR. NO BARCODE FELL OFF THE CELLS AND NO MIXING OF TWO TYPES OF BARCODE NUCLEIC ACIDS WAS OBSERVED.
C: VISUALIZE BARCODE A
D: VISUALIZE BARCODE B

FIG. 6

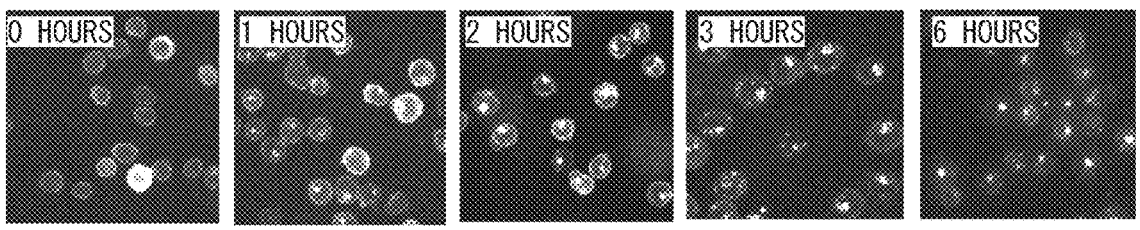

A: FORMALIN FIXATION, WITHOUT LPS (DMSO ONLY)
B: FORMALIN FIXATION, WITH LPS
C: DTSSP FIXATION, WITHOUT LPS (DMSO ONLY)
D: DTSSP FIXATION, WITH LPS

FIG. 12A

TABLE 1-1

| SECOND COMMON BARCODE REGION | NUMBER OF READS OF FIRST BARCODE NUCLEIC ACID A | NUMBER OF READS OF FIRST BARCODE NUCLEIC ACID B |
|---|---|---|
| AATCGACCAACTGTGT | 3363 | 0 |
| ACTATCTTCGATTCCC | 2463 | 0 |
| AATTCCTAGCCAGAGT | 772 | 0 |
| AAAGTCCGTAAGCGGT | 691 | 0 |
| AAACGCTGTACTCGAT | 545 | 0 |
| AATGACCAGGGTCTTT | 310 | 0 |
| ACAGGGACAGCGAACA | 297 | 0 |
| ACCATTTAGCGCTGCT | 292 | 0 |
| AATCGTGCAATTTCGG | 287 | 0 |
| AAAGGTACACATGGTT | 23 | 255 |
| AACAAAGGTTCCTTGC | 243 | 0 |
| ACATGCAGTTCTGAGT | 242 | 0 |
| ACGCACGTCGGCCTTT | 219 | 0 |
| ACTCTCGAGAGATCGC | 216 | 0 |
| ACCAAACAGCTTCGTA | 191 | 0 |
| ACCAAACTCACTGGGC | 178 | 0 |
| AATTTCCTCGAATCCA | 172 | 0 |
| ACGTAACTCTCAACGA | 153 | 0 |
| ACACGCGTCCATCTAT | 152 | 0 |
| AAACCCACAGAGACTG | 151 | 0 |
| ACATCCCCACGACGTC | 2 | 147 |
| ACGATCAGTGACTGAG | 137 | 0 |
| AAGCATCAGCGTCGAA | 136 | 0 |
| AACCTGACACAACATC | 126 | 0 |
| ACCCTTGAGGCATTTC | 123 | 0 |
| AAAGGGCTCCATGATG | 116 | 0 |
| ACTGTCCAGAGACAAG | 113 | 0 |
| AAGCGAGGTAGAAACT | 112 | 0 |
| AAGCGTTAGATAGCTA | 104 | 0 |
| AACCTTTAGAGCAACC | 103 | 0 |
| ACCACAAAGTAACAGT | 103 | 0 |
| ACATTTCAGAACTCCT | 100 | 0 |
| AACAGGGGTAGCACGA | 85 | 0 |
| AAACGCTAGAAGGATG | 84 | 0 |
| AAATGGACATAACAGA | 84 | 0 |
| AAACGAATCATCTATC | 78 | 0 |
| AATGAAGTCTAACGCA | 77 | 0 |
| ACCTGTCAGTTGGGAC | 77 | 0 |
| ACAGAAACAATTAGGA | 72 | 0 |
| ACTGCAAGTGTTCCAA | 72 | 0 |
| AAAGGGCGTAGACTGG | 69 | 0 |
| ACCGTTCAGTACGTCT | 69 | 0 |
| ACTATCTTCACGACTA | 65 | 0 |
| AAGCATCTCAATGTCG | 64 | 0 |
| AATGACCTCTCCTGAC | 64 | 0 |
| ACTATGGCAGTTGTCA | 62 | 0 |
| AATGAAGTCGAATGCT | 58 | 0 |
| ACACGCGTCACAAGGG | 58 | 0 |
| AAGACTCCAGCTGTGC | 56 | 0 |
| ACAGAAACAAGTTTGC | 56 | 0 |
| AAACGCTGTATGGAGC | 54 | 0 |
| AATGCCAGTGTAAACA | 54 | 0 |
| ACGATCACAACGTTAC | 54 | 0 |
| AATTCCTTCCCAACTC | 53 | 0 |
| ACACCAAGTCACTGAT | 53 | 0 |
| ACCAACAGTGGGATTG | 52 | 0 |
| ACGTCCTGTTACCTTT | 1 | 51 |
| AAGAACACAGTTTCAG | 51 | 0 |
| AAGTCGTTCTCTTAAC | 51 | 0 |

FIG. 12B

TABLE 1-2

| SECOND COMMON BARCODE REGION | NUMBER OF READS OF FIRST BARCODE NUCLEIC ACID A | NUMBER OF READS OF FIRST BARCODE NUCLEIC ACID B |
|---|---|---|
| ACACGCGTCCTAAACG | 51 | 0 |
| ACAGAAAAGTATCTGC | 51 | 0 |
| ACCCTCAAGATACCAA | 51 | 0 |
| AACACACAGTTCATCG | 49 | 0 |
| AACCTTTGTCTGTGAT | 49 | 0 |
| ACGATGTGTACAAGTA | 49 | 0 |
| AAACGCTTCGTTGTGA | 47 | 0 |
| ACATTTCGTCGGAAAC | 47 | 0 |
| AACAGGGGTGTCTTCC | 44 | 0 |
| ACATGCAGTCACAGTT | 44 | 0 |
| ACCACAACACTTTATC | 44 | 0 |
| ACCATTTCATCTGGGC | 43 | 0 |
| AAGTTCGAGAGGGTAA | 42 | 0 |
| ACATCGAGTGTTGATC | 42 | 0 |
| ACGATCAGTTCGGTTA | 41 | 1 |
| ACGTTCCCACGACGAA | 42 | 0 |
| AAAGTCCGTAGTCCTA | 41 | 0 |
| AACCAACAGCCATGCC | 41 | 0 |
| AATCACGGTGCTGCAC | 41 | 0 |
| AAGATAGAGTAGTGCG | 40 | 0 |
| ACACGCGTCTGAGAAA | 40 | 0 |
| AAAGGGCGTGCATTTG | 39 | 0 |
| ACACAGTAGCTCACTA | 39 | 0 |
| ACATCGATCTCACCCA | 39 | 0 |
| ACATTTCTCGATAACC | 39 | 0 |
| ACCATTTGTCTCTCCA | 39 | 0 |
| ACGTTCCGTCGATTAC | 38 | 0 |
| AAAGGGCAGCGGTAGT | 36 | 1 |
| AAAGTCCAGCCATGCC | 37 | 0 |
| AACAAGACAAGCGATG | 37 | 0 |
| ACCCAAACAGCTCATA | 37 | 0 |
| ACACGCGCACCAAAGG | 35 | 0 |
| ACATGCATCACCGGGT | 35 | 0 |
| ACTACGAAGGATATGT | 35 | 0 |
| ACGTACACAATCAAGA | 34 | 0 |
| ACCAAACTCCCATGGG | 33 | 0 |
| ACTGTGAGTACTTGTG | 33 | 0 |
| ACGTTCCCATCACCAA | 32 | 0 |
| ACTACGATCCATGAGT | 32 | 0 |
| AAGCCATAGCGTCAGA | 0 | 31 |
| ACCATTTCATAGAATG | 31 | 0 |

FIG. 14A

TABLE 2-1

| SECOND COMMON BARCODE REGION | NUMBER OF READS OF FIRST BARCODE NUCLEIC ACID A | NUMBER OF READS OF FIRST BARCODE NUCLEIC ACID B |
|---|---|---|
| ACCCTTGCATGGTACT | 0 | 2649 |
| ACGTAACAGGATTACA | 0 | 1436 |
| ACTCTCGTCACAGTGT | 0 | 1359 |
| AATGGCTTCTGAGCAT | 0 | 1058 |
| AAGTGAATCCGGACTG | 0 | 543 |
| AATGAAGCAAGGTCAG | 0 | 345 |
| AATGGAACACAGTCGC | 0 | 302 |
| ACTTATCGTTTGAACC | 1 | 272 |
| AAGACAAGTCAGGTAG | 0 | 263 |
| AAACCCAAGGAAGAAC | 0 | 165 |
| ACCAACAAGGTACTGG | 0 | 141 |
| AATCACGAGCTCCATA | 0 | 139 |
| ACCTGAAGTTCAAGTC | 0 | 117 |
| AAACCCAGTTACGATC | 0 | 93 |
| AATAGAGCAGCTCGGT | 1 | 90 |
| ACACCAAAGCCTGAAG | 0 | 91 |
| AAATGGACAATTGCAC | 0 | 78 |
| ACACTGATCTCTGACC | 0 | 78 |
| AACAAGAAGCGCCATC | 0 | 73 |
| ACCTGAAAGAATCGCG | 0 | 68 |
| ACCAACACAGGGAATC | 0 | 64 |
| AACGAAAGTGGAAGTC | 0 | 63 |
| AATGGCTTCCGTTGAA | 0 | 61 |
| ACGATCATCCTCACTG | 0 | 61 |
| AACAAAGTCATATGGC | 0 | 57 |
| AACAACCGTCTGTGCG | 0 | 56 |
| ACCAACATCCGAAGGA | 0 | 54 |
| AATTCCTCAGTTTCAG | 0 | 52 |
| ACTCCCAGTCAGCGTC | 0 | 52 |
| ACCCAAAAGTGTGTTC | 0 | 46 |
| ACATGCAGTACGAAAT | 0 | 41 |
| AAGTGAAGTCAGTCTA | 0 | 40 |
| ACACGCGCATGACGTT | 0 | 40 |
| ACATTTCTCATTTCCA | 0 | 39 |
| AAAGGGCCATCCGAAT | 0 | 34 |
| AAAGAACAGTTAGAAC | 0 | 33 |
| AAGCGAGAGCAGTACG | 0 | 33 |
| AAGTGAACAAAGCTAA | 0 | 33 |
| ACTGTCCTCTGGAGAG | 0 | 33 |
| ACTTCCGGTCAGGTAG | 0 | 32 |
| AAGGAATGTGTCCTAA | 0 | 31 |
| AAAGGTAAGACTCTTG | 0 | 29 |

FIG. 14B

TABLE 2-2

| SECOND COMMON BARCODE REGION | NUMBER OF READS OF FIRST BARCODE NUCLEIC ACID A | NUMBER OF READS OF FIRST BARCODE NUCLEIC ACID B |
|---|---|---|
| AACACACTCTTTGCGC | 0 | 28 |
| ACCGTTCGTAGGGAGG | 0 | 28 |
| ACGCACGAGCATGTTC | 0 | 28 |
| ACTACGACAGTGCGCT | 0 | 28 |
| AACAACCGTTCGGTAT | 0 | 27 |
| AATGCCACAGACTCTA | 0 | 27 |
| ACATCGAGTCTTCAAG | 0 | 27 |
| AAGACAACAAATCCCA | 0 | 26 |
| AATTCCTAGATTGCGG | 0 | 26 |
| AAGTCGTAGACGTCCC | 0 | 25 |
| ACAACCACAACGTTAC | 0 | 25 |
| ACGGTTATCGCCGATG | 0 | 25 |
| ACTTTGTAGTATTAGG | 0 | 25 |
| AAACCCAAGGGCGAGA | 0 | 24 |
| AAACGCTCAGCCGTTG | 0 | 24 |
| AACCTGAAGATGATTG | 0 | 24 |
| AATCGACTCTAGCCAA | 0 | 24 |
| ACACTGACATACAGAA | 0 | 24 |
| AACGTCACACTTCATT | 0 | 23 |
| AATGAAGCAAGATGGC | 0 | 23 |
| AATGGCTGTAGTAAGT | 1 | 22 |
| AATGGCTTCATGAGGG | 0 | 23 |
| AATGCCACATAGATGA | 0 | 22 |
| ACAGCCGAGTTCCATG | 0 | 22 |
| ACATCCCCAGCGCTTG | 1 | 21 |
| AACAGGGTCGATGGAG | 0 | 21 |
| AACTTCTTCTTTCCAA | 0 | 21 |
| AAGTCGTAGGTTCAGG | 0 | 21 |
| AAGTTCGTCTCGTGGG | 0 | 21 |
| AATGAAGAGAGAATCT | 0 | 21 |
| ACTCTCGTCCTCGCAT | 0 | 21 |
| AACCACATCCTATTTG | 0 | 20 |
| AAGCGAGTCACTCTTA | 0 | 20 |
| AAGTACCTCCGGACGT | 0 | 20 |
| ACCACAAGTTGGTAGG | 0 | 20 |
| ACTACGATCCACTTCG | 0 | 20 |
| ACTATTCTCGCCTATC | 0 | 20 |
| AACAAGAGTGAGGAAA | 0 | 19 |
| AACCACATCGGTTCAA | 0 | 19 |
| AAGATAGAGCTATCCA | 0 | 18 |
| AAGCCATTCTGCTTAT | 0 | 18 |
| ACACCAAAGACCATAA | 0 | 18 |
| ACCAACACATTCGGGC | 0 | 18 |
| ACCTGAACATTCGGGC | 0 | 18 |
| AAACGAAAGCTCGTGC | 0 | 17 |
| AACCTGACATCACCAA | 0 | 17 |
| AACCTTTAGAGATTCA | 0 | 17 |
| AATTCCTCAGCAGAAC | 0 | 17 |
| AATTCCTTCCACGTCT | 0 | 17 |
| AAGACAAGTACTGGGA | 0 | 16 |
| AATGGCTAGTATGCAA | 0 | 16 |
| AATTTCCGTAGGAAAG | 0 | 16 |
| ACAACCACAAGGGTCA | 0 | 16 |
| ACATCCCAGTCCCGAC | 0 | 16 |
| ACATCCCTCCTCTGCA | 0 | 16 |
| ACCTGTCTCCCGAGGT | 0 | 16 |
| ACGATCAAGCAACTCT | 0 | 16 |

GRAPH 2

FIG. 19

| barcode # | | | | compounds | function |
|---|---|---|---|---|---|
| 30 uM | 10uM | 3 uM | 1 uM | | |
| 1 | 25 | 49 | 73 | TAK242 | selectively binds to Cys747 of TLR4 and selectively disrupts its interaction with adaptor molecules TIRAP and TRAM. |
| 2 | 26 | 50 | 74 | Selisistat (EX 527) | a potent and selective SIRT1 inhibitor |
| 3 | 27 | 51 | 75 | Cyproterone Acetate | androgen receptor (AR) antagonist |
| 4 | 28 | 52 | 76 | Pioglitazone HCl | a selective peroxisome proliferator-activated receptor-gamma (PPARγ) agonist |
| 5 | 29 | 53 | 77 | Phlorizin | a competitive inhibitor of SGLT1 and SGLT2 |
| 6 | 30 | 54 | 78 | BMY 7378 Dihydrochloride | a multi-targeted inhibitor of α2C-adrenoceptor and α1D-adrenoceptor |
| 7 | 31 | 55 | 79 | Camostat Mesilate | a trypsin-like protease inhibitor, inhibits airway epithelial sodium channel (ENaC) |
| 8 | 32 | 56 | 80 | Tempol | a superoxide scavenger that displays neuroprotective, anti-inflammatory and analgesic effects |
| 9 | 33 | 57 | 81 | U-104 | a potent carbonic anhydrase (CA) inhibitor |
| 10 | 34 | 58 | 82 | T0070907 | a potent and selective PPARγ inhibitor |
| 11 | 35 | 59 | 83 | Roxadustat (FG-4592) | an oral inhibitor of hypoxia inducible factor (HIF) prolyl hydroxylase |
| 12 | 36 | 60 | 84 | Vatalanib (PTK787) 2HCl | an inhibitor of VEGFR2/KDR |
| 13 | 37 | 61 | 85 | Fulvestrant | an estrogen receptor (ER) antagonist |
| 14 | 38 | 62 | 86 | Temozolomide | A DNA damage inducer |
| 15 | 39 | 63 | 87 | SB525334 | a potent and selective inhibitor of TGFβ receptor I (ALK5) |
| 16 | 40 | 64 | 88 | AG-1478 (Tyrphostin AG-1478) | selective EGFR inhibitor |
| 17 | 41 | 65 | 89 | VX-702 | a highly selective inhibitor of p38α MAPK |
| 18 | 42 | 66 | 90 | 2-Methoxyestradiol (2-MeOE2) | depolymerizes microtubules and blocks HIF-1α nuclear accumulation and HIF-transcriptional activity. |
| 19 | 43 | 67 | 91 | Costunolide | inhibits farnesyl-protein transferase (FPTase) |
| 20 | 44 | 68 | 92 | Naftopidil DiHCl | a selective 5-HT1A and α1-adrenergic receptor antagonist |
| 21 | 45 | 69 | 93 | Droxinostat | a selective inhibitor of HDAC, mostly for HDACs 6 and 8 |
| 22 | 46 | 70 | 94 | Nevirapine | a non-nucleoside reverse transcriptase inhibitor (NNRTI) |
| 23 | 47 | 71 | 95 | Flutamide | an antiandrogen drug, with its active metabolite binding at androgen receptor |
| 24 | 48 | 72 | 96 | Nefiracetam | a GABAergic, cholinergic, and monoaminergic neuronal system enhancer for Ro 5-4864-induced convulsions. |

FIG. 20A

| barcode# | FIRST BARCODE NUCLEIC ACID |
|---|---|
| Ind_8bp_001 | CCTTGGCACCCGAGAATTCCACCTGAACCAAAAAAAAAAAAAAAAAAAAAAAAAAAAAA |
| Ind_8bp_002 | CCTTGGCACCCGAGAATTCCATATCCAGTAAAAAAAAAAAAAAAAAAAAAAAAAAAAAA |
| Ind_8bp_003 | CCTTGGCACCCGAGAATTCCAGAGATAACAAAAAAAAAAAAAAAAAAAAAAAAAAAAAA |
| Ind_8bp_005 | CCTTGGCACCCGAGAATTCCAAGCCTACTAAAAAAAAAAAAAAAAAAAAAAAAAAAAAA |
| Ind_8bp_006 | CCTTGGCACCCGAGAATTCCAATGCACCTAAAAAAAAAAAAAAAAAAAAAAAAAAAAAA |
| Ind_8bp_007 | CCTTGGCACCCGAGAATTCCACATGGAATAAAAAAAAAAAAAAAAAAAAAAAAAAAAAA |
| Ind_8bp_008 | CCTTGGCACCCGAGAATTCCACAGTTCCAAAAAAAAAAAAAAAAAAAAAAAAAAAAAAA |
| Ind_8bp_009 | CCTTGGCACCCGAGAATTCCACCGTATATAAAAAAAAAAAAAAAAAAAAAAAAAAAAAA |
| Ind_8bp_010 | CCTTGGCACCCGAGAATTCCAGCTGAAGAAAAAAAAAAAAAAAAAAAAAAAAAAAAAAA |
| Ind_8bp_0012 | CCTTGGCACCCGAGAATTCCACGCAAGCTAAAAAAAAAAAAAAAAAAAAAAAAAAAAAA |
| Ind_8bp_013 | CCTTGGCACCCGAGAATTCCATATCTGTGAAAAAAAAAAAAAAAAAAAAAAAAAAAAAA |
| Ind_8bp_014 | CCTTGGCACCCGAGAATTCCAGCCGAATGAAAAAAAAAAAAAAAAAAAAAAAAAAAAAA |
| Ind_8bp_015 | CCTTGGCACCCGAGAATTCCATACTGCAGAAAAAAAAAAAAAAAAAAAAAAAAAAAAAA |
| Ind_8bp_016 | CCTTGGCACCCGAGAATTCCACATGTTGAAAAAAAAAAAAAAAAAAAAAAAAAAAAAAA |
| Ind_8bp_017 | CCTTGGCACCCGAGAATTCCAATAGAGTCAAAAAAAAAAAAAAAAAAAAAAAAAAAAAA |
| Ind_8bp_018 | CCTTGGCACCCGAGAATTCCATAACCTCAAAAAAAAAAAAAAAAAAAAAAAAAAAAAAA |
| Ind_8bp_019 | CCTTGGCACCCGAGAATTCCAATTAGCTGAAAAAAAAAAAAAAAAAAAAAAAAAAAAAA |
| Ind_8bp_020 | CCTTGGCACCCGAGAATTCCATCACGCTCAAAAAAAAAAAAAAAAAAAAAAAAAAAAAA |
| Ind_8bp_021 | CCTTGGCACCCGAGAATTCCAGCATCACGAAAAAAAAAAAAAAAAAAAAAAAAAAAAAA |
| Ind_8bp_022 | CCTTGGCACCCGAGAATTCCACTGAATCAAAAAAAAAAAAAAAAAAAAAAAAAAAAAAA |
| Ind_8bp_023 | CCTTGGCACCCGAGAATTCCAAGGACGGTAAAAAAAAAAAAAAAAAAAAAAAAAAAAAA |
| Ind_8bp_024 | CCTTGGCACCCGAGAATTCCAGAACGTAGAAAAAAAAAAAAAAAAAAAAAAAAAAAAAA |
| Ind_8bp_025 | CCTTGGCACCCGAGAATTCCATGTCACCGAAAAAAAAAAAAAAAAAAAAAAAAAAAAAA |
| Ind_8bp_026 | CCTTGGCACCCGAGAATTCCAACCTTGAAAAAAAAAAAAAAAAAAAAAAAAAAAAAAAA |
| Ind_8bp_027 | CCTTGGCACCCGAGAATTCCAGTGGTTCCAAAAAAAAAAAAAAAAAAAAAAAAAAAAAA |
| Ind_8bp_028 | CCTTGGCACCCGAGAATTCCATATGGTGTAAAAAAAAAAAAAAAAAAAAAAAAAAAAAA |
| Ind_8bp_031 | CCTTGGCACCCGAGAATTCCACTGGCTCTAAAAAAAAAAAAAAAAAAAAAAAAAAAAAA |
| Ind_8bp_032 | CCTTGGCACCCGAGAATTCCAGGCTCTTGAAAAAAAAAAAAAAAAAAAAAAAAAAAAAA |
| Ind_8bp_033 | CCTTGGCACCCGAGAATTCCACGAACAGTAAAAAAAAAAAAAAAAAAAAAAAAAAAAAA |
| Ind_8bp_034 | CCTTGGCACCCGAGAATTCCAGGTTAGCAAAAAAAAAAAAAAAAAAAAAAAAAAAAAAA |
| Ind_8bp_035 | CCTTGGCACCCGAGAATTCCAAGACGCTGAAAAAAAAAAAAAAAAAAAAAAAAAAAAAA |
| Ind_8bp_036 | CCTTGGCACCCGAGAATTCCATTGCTAGGAAAAAAAAAAAAAAAAAAAAAAAAAAAAAA |

FIG. 20B

| barcode# | FIRST BARCODE NUCLEIC ACID |
|---|---|
| Ind_8bp_037 | CCTTGGCACCCGAGAATTCCACTCCGGTTAAAAAAAAAAAAAAAAAAAAAAAAAAAA |
| Ind_8bp_038 | CCTTGGCACCCGAGAATTCCACACCTCAGAAAAAAAAAAAAAAAAAAAAAAAAAAAA |
| Ind_8bp_039 | CCTTGGCACCCGAGAATTCCACGTAATAGAAAAAAAAAAAAAAAAAAAAAAAAAAAA |
| Ind_8bp_040 | CCTTGGCACCCGAGAATTCCAGTTAATGCAAAAAAAAAAAAAAAAAAAAAAAAAAAA |
| Ind_8bp_041 | CCTTGGCACCCGAGAATTCCATCTAAGGAAAAAAAAAAAAAAAAAAAAAAAAAAAAA |
| Ind_8bp_042 | CCTTGGCACCCGAGAATTCCACGAACTTCAAAAAAAAAAAAAAAAAAAAAAAAAAAA |
| Ind_8bp_045 | CCTTGGCACCCGAGAATTCCAATTACCGAAAAAAAAAAAAAAAAAAAAAAAAAAAAA |
| Ind_8bp_047 | CCTTGGCACCCGAGAATTCCAAGTTGTTGAAAAAAAAAAAAAAAAAAAAAAAAAAAA |
| Ind_8bp_048 | CCTTGGCACCCGAGAATTCCAACGCTGTCAAAAAAAAAAAAAAAAAAAAAAAAAAAA |
| Ind_8bp_049 | CCTTGGCACCCGAGAATTCCAATTGGCAAAAAAAAAAAAAAAAAAAAAAAAAAAAAA |
| Ind_8bp_051 | CCTTGGCACCCGAGAATTCCACTAGGATTAAAAAAAAAAAAAAAAAAAAAAAAAAAA |
| Ind_8bp_052 | CCTTGGCACCCGAGAATTCCATGAAGGATAAAAAAAAAAAAAAAAAAAAAAAAAAAA |
| Ind_8bp_053 | CCTTGGCACCCGAGAATTCCAAGTCCGAAAAAAAAAAAAAAAAAAAAAAAAAAAAAA |
| Ind_8bp_054 | CCTTGGCACCCGAGAATTCCACATACTCTAAAAAAAAAAAAAAAAAAAAAAAAAAAA |
| Ind_8bp_055 | CCTTGGCACCCGAGAATTCCATTCAGTAGAAAAAAAAAAAAAAAAAAAAAAAAAAAA |
| Ind_8bp_058 | CCTTGGCACCCGAGAATTCCAAGGATGCCAAAAAAAAAAAAAAAAAAAAAAAAAAAA |
| Ind_8bp_059 | CCTTGGCACCCGAGAATTCCAAGGAATGGAAAAAAAAAAAAAAAAAAAAAAAAAAAA |
| Ind_8bp_060 | CCTTGGCACCCGAGAATTCCAACCACCACAAAAAAAAAAAAAAAAAAAAAAAAAAAA |
| Ind_8bp_061 | CCTTGGCACCCGAGAATTCCATTGCATGTAAAAAAAAAAAAAAAAAAAAAAAAAAAA |
| Ind_8bp_062 | CCTTGGCACCCGAGAATTCCACGATACGCAAAAAAAAAAAAAAAAAAAAAAAAAAAA |
| Ind_8bp_063 | CCTTGGCACCCGAGAATTCCATGTTCTCGAAAAAAAAAAAAAAAAAAAAAAAAAAAA |
| Ind_8bp_064 | CCTTGGCACCCGAGAATTCCATTCCTCCGAAAAAAAAAAAAAAAAAAAAAAAAAAAA |
| Ind_8bp_065 | CCTTGGCACCCGAGAATTCCATCTCTATCAAAAAAAAAAAAAAAAAAAAAAAAAAAA |
| Ind_8bp_066 | CCTTGGCACCCGAGAATTCCACACTCTCCAAAAAAAAAAAAAAAAAAAAAAAAAAAA |
| Ind_8bp_067 | CCTTGGCACCCGAGAATTCCACGCTTCTGAAAAAAAAAAAAAAAAAAAAAAAAAAAA |
| Ind_8bp_068 | CCTTGGCACCCGAGAATTCCATCCGTCAAAAAAAAAAAAAAAAAAAAAAAAAAAAAA |
| Ind_8bp_069 | CCTTGGCACCCGAGAATTCCACTTGCCTCAAAAAAAAAAAAAAAAAAAAAAAAAAAA |
| Ind_8bp_070 | CCTTGGCACCCGAGAATTCCACCTGTATGAAAAAAAAAAAAAAAAAAAAAAAAAAAA |
| Ind_8bp_071 | CCTTGGCACCCGAGAATTCCAGAACGATTAAAAAAAAAAAAAAAAAAAAAAAAAAAA |
| Ind_8bp_072 | CCTTGGCACCCGAGAATTCCAAGGTCTCCAAAAAAAAAAAAAAAAAAAAAAAAAAAA |
| Ind_8bp_073 | CCTTGGCACCCGAGAATTCCAGGTGTCTTAAAAAAAAAAAAAAAAAAAAAAAAAAAA |
| Ind_8bp_074 | CCTTGGCACCCGAGAATTCCATGTACGACAAAAAAAAAAAAAAAAAAAAAAAAAAAA |

FIG. 20C

| barcode# | FIRST BARCODE NUCLEIC ACID |
|---|---|
| Ind_8bp_075 | CCTTGGCACCCGAGAATTCCACTGTAAGTAAAAAAAAAAAAAAAAAAAAAAAAAAAAA |
| Ind_8bp_076 | CCTTGGCACCCGAGAATTCCATCAGGTACAAAAAAAAAAAAAAAAAAAAAAAAAAAAA |
| Ind_8bp_077 | CCTTGGCACCCGAGAATTCCAATCCGACGAAAAAAAAAAAAAAAAAAAAAAAAAAAAA |
| Ind_8bp_078 | CCTTGGCACCCGAGAATTCCAGCAAGAAGAAAAAAAAAAAAAAAAAAAAAAAAAAAAA |
| Ind_8bp_079 | CCTTGGCACCCGAGAATTCCAACGTAGCCAAAAAAAAAAAAAAAAAAAAAAAAAAAAA |
| Ind_8bp_081 | CCTTGGCACCCGAGAATTCCACCAGTCACAAAAAAAAAAAAAAAAAAAAAAAAAAAAA |
| Ind_8bp_082 | CCTTGGCACCCGAGAATTCCAGGCTTCAAAAAAAAAAAAAAAAAAAAAAAAAAAAA |
| Ind_8bp_085 | CCTTGGCACCCGAGAATTCCAGAATTCTCAAAAAAAAAAAAAAAAAAAAAAAAAAAAA |
| Ind_8bp_087 | CCTTGGCACCCGAGAATTCCATCCACACCAAAAAAAAAAAAAAAAAAAAAAAAAAAAA |
| Ind_8bp_090 | CCTTGGCACCCGAGAATTCCACGCCACTTAAAAAAAAAAAAAAAAAAAAAAAAAAAAA |
| Ind_8bp_091 | CCTTGGCACCCGAGAATTCCAGAACACCGAAAAAAAAAAAAAAAAAAAAAAAAAAAAA |
| Ind_8bp_093 | CCTTGGCACCCGAGAATTCCACTGGACAAAAAAAAAAAAAAAAAAAAAAAAAAAAAA |
| Ind_8bp_100 | CCTTGGCACCCGAGAATTCCATCGCCAGAAAAAAAAAAAAAAAAAAAAAAAAAAAAAA |
| Ind_8bp_104 | CCTTGGCACCCGAGAATTCCAGACTCGCAAAAAAAAAAAAAAAAAAAAAAAAAAAAAA |
| Ind_8bp_113 | CCTTGGCACCCGAGAATTCCATACATCTGAAAAAAAAAAAAAAAAAAAAAAAAAAAAA |
| Ind_8bp_118 | CCTTGGCACCCGAGAATTCCAGAGATTGTAAAAAAAAAAAAAAAAAAAAAAAAAAAAA |
| Ind_8bp_134 | CCTTGGCACCCGAGAATTCCAAACTGAGCAAAAAAAAAAAAAAAAAAAAAAAAAAAAA |
| Ind_8bp_135 | CCTTGGCACCCGAGAATTCCAAACACATCAAAAAAAAAAAAAAAAAAAAAAAAAAAAA |
| Ind_8bp_147 | CCTTGGCACCCGAGAATTCCAATATGGGAAAAAAAAAAAAAAAAAAAAAAAAAAAAAA |
| Ind_8bp_157 | CCTTGGCACCCGAGAATTCCATTACCGGGAAAAAAAAAAAAAAAAAAAAAAAAAAAAA |
| Ind_8bp_162 | CCTTGGCACCCGAGAATTCCAGAAGCGATAAAAAAAAAAAAAAAAAAAAAAAAAAAAA |
| Ind_8bp_168 | CCTTGGCACCCGAGAATTCCAAAAGGGTAAAAAAAAAAAAAAAAAAAAAAAAAAAAAA |
| Ind_8bp_183 | CCTTGGCACCCGAGAATTCCAGGCTAAGAAAAAAAAAAAAAAAAAAAAAAAAAAAAAA |
| Ind_8bp_198 | CCTTGGCACCCGAGAATTCCAGTCGGGAAAAAAAAAAAAAAAAAAAAAAAAAAAAAA |
| Ind_8bp_199 | CCTTGGCACCCGAGAATTCCAGTACAGGAAAAAAAAAAAAAAAAAAAAAAAAAAAAAA |
| Ind_8bp_208 | CCTTGGCACCCGAGAATTCCAACATAGGTAAAAAAAAAAAAAAAAAAAAAAAAAAAAA |
| Ind_8bp_212 | CCTTGGCACCCGAGAATTCCAGCTAGGGTAAAAAAAAAAAAAAAAAAAAAAAAAAAAA |
| Ind_8bp_224 | CCTTGGCACCCGAGAATTCCAACGGCGATAAAAAAAAAAAAAAAAAAAAAAAAAAAAA |
| Ind_8bp_238 | CCTTGGCACCCGAGAATTCCAGGATGAAAAAAAAAAAAAAAAAAAAAAAAAAAAAAA |
| Ind_8bp_245 | CCTTGGCACCCGAGAATTCCATCGTTTGAAAAAAAAAAAAAAAAAAAAAAAAAAAAAA |
| Ind_8bp_254 | CCTTGGCACCCGAGAATTCCAGAGGGACAAAAAAAAAAAAAAAAAAAAAAAAAAAAAA |
| Ind_8bp_262 | CCTTGGCACCCGAGAATTCCATCGGTTTCAAAAAAAAAAAAAAAAAAAAAAAAAAAAA |

CELLULAR PHENOTYPE SCREENING METHOD

TECHNICAL FIELD

This patent application claims priority based on United States Patent Application, Publication No. 62/959,420, filed Jan. 10, 2020, and the contents of the entire disclosure in this prior patent application are included by reference as a part of the disclosure of the present specification.

The present disclosure relates to novel cellular phenotype screening.

BACKGROUND ART

Cellular phenotype (phenotype screening) is known as a screening method to screen various drugs using cells. Phenotype screening is a method of searching for drugs (for example, low molecular weight compounds, peptides, or the like) which change phenotypes of cells and organs, using the phenotypes of cells and organs, for example, cell proliferation rate, cell death, and cell image information represented by the localization of specific proteins or cell structure, as indicators. One of the important objectives of cellular phenotype screening is to examine the information regarding (i) what kind of cellular phenotype change is exhibited (image response), (ii) the gene expression response exhibited, and (iii) the mechanism of action which is the basis thereof, in respect to an input (test substance, drug stimulation, or the like).

However, in the general large-scale phenotypic screening assay systems using wells of the related art, it is necessary to apply each drug to cells cultured in each well, examine the image response, and then take out objects in which a response thought to be the target phenotype was produced and conduct genetic analysis of the individual subjects to find out the gene expression response and mechanism of action (for example, Non-Patent Document 1 and the like). Accordingly, in addition to being slow and incurring high costs, it was difficult to quickly perform multifaceted analysis of the gene expression response, mechanism of action, and the like with respect to individual cells.

CITATION LIST

Non-Patent Document

[Non-Patent Document 1]
Nature Methods, volume 16, pages 619 to 626 (2019)

SUMMARY OF INVENTION

The present disclosure provides a method for rapidly detecting image responses and gene expression responses for cells coexisting with test targets such as drugs.

According to an embodiment of the present disclosure, there is provided a method for screening test targets, the method including a step of preparing a plurality of cells which are tagged with a first barcode nucleic acid associated with a test target and treated with the test targets, a step of sorting the plurality of cells based on a cellular phenotype using an imaging cell sorter, and a step of identifying the test targets used to treat each cell using the first barcode nucleic acids as indicators.

According to the present disclosure, it is possible to rapidly detect image responses and gene expression responses for cells coexisting with test targets. According to the present disclosure, each input information, such as the treatment performed on the cells by the test objects, is associated with the image responses and the gene expression responses in a pooled state, and is able to be advantageously used when performing phenotypic screening at high speed. It is possible to advantageously use the present disclosure in selecting or searching for test targets which cause desired phenotypic changes in cells.

BRIEF DESCRIPTION OF DRAWINGS

FIG. 4 is fluorescent micrographs of cells after addition of red fluorescent dye Cy5 conjugated oligonucleotides (having a sequence corresponding to a partial sequence of the first barcode nucleic acid) and incubation in each solution for 30 minutes.

FIG. 5 is fluorescent micrographs of the cell samples. Cells tagged with green fluorescent dye FAM conjugated oligonucleotides (having a sequence corresponding to a partial sequence of the first barcode nucleic acid) and cells tagged with red fluorescent dye Cy5 conjugated oligonucleotides (having a sequence corresponding to a partial sequence of the first barcode nucleic acid) were prepared and mixed with each other. The photographs were taken after one hour incubation.

FIG. 6 is photographs when the attachment of oligonucleotides to the cells is observed over time in the cells to which red fluorescent dye Cy5 conjugated oligonucleotides (having a sequence corresponding to a partial sequence of the first barcode nucleic acid) are attached.

FIG. 12A is a table (Table 1-1) representing the second common barcode region sequence of each cell in a mixed sample (the ratio of cells where the LPS drug was present to where the drug was absent was 9:1) and the number of reads of each first barcode sequence detected from unique reads having the above.

FIG. 12B is another table (Table 1-2) representing the second common barcode region sequence of each cell in a mixed sample (the ratio of cells where the LPS drug was present to where the drug was absent was 9:1) and the number of reads of each first barcode sequence detected from the unique reads having the above.

FIG. 14A is a table (Table 2-1) representing the second common barcode region sequence of each negative control cell where the LPS drug was absent and the number of reads of each first barcode region sequence detected from the unique reads having the above.

FIG. 14B is a table (Table 2-2) representing the second common barcode region sequence of each negative control cell where the LPS drug was absent and the number of reads of each first barcode region sequence detected from the unique reads having the above.

FIG. 19 is a table showing the 96 types of test targets (24 types of test substances ×4 types of concentrations) and the functions (known mechanisms of action) of the test substances used in Example 8.

FIG. 20A is a table showing the sequences of the first barcode nucleic acids (Barcode #: lnd_8 bp_0015-lnd_8 bp_036) which specify the test targets used in Example 8.

FIG. 20B is a table showing the sequences of the first barcode nucleic acids (Barcode #: lnd_8 bp_037-lnd_8 bp_074) used in Example 8.

FIG. 20C is a table showing the sequences of the first barcode nucleic acids (Barcode #: lnd_8 bp_075-lnd_8 bp_262) used in Example 8.

DESCRIPTION OF EMBODIMENTS

Figure 1:
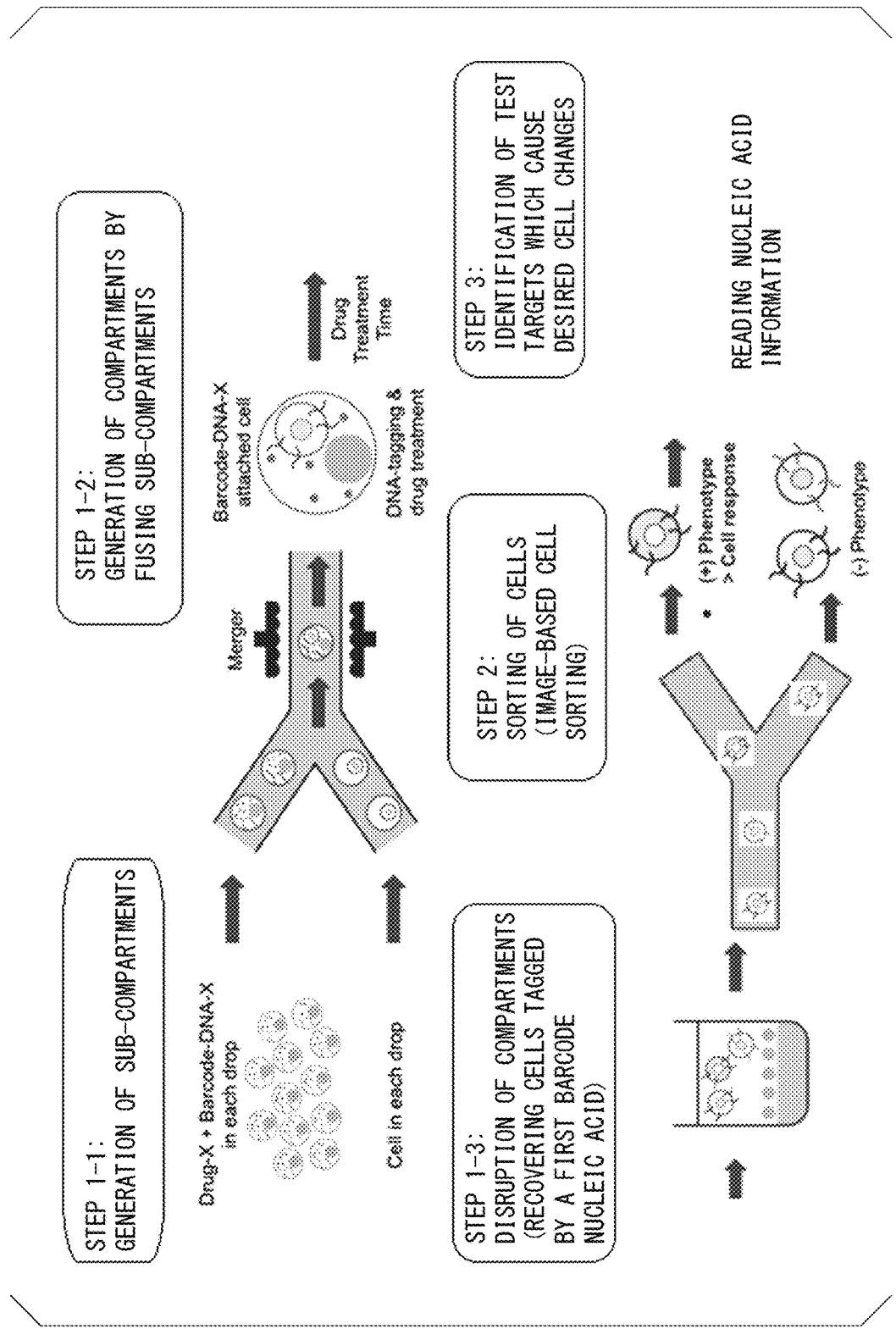
FIG. 1 is a schematic diagram of an embodiment of a screening method of the present disclosure.

According to an embodiment of the present disclosure, a method for screening a cell includes a step of preparing a plurality of cells which are tagged with a first barcode nucleic acid associated with a test target and treated with the test target, a step of sorting the plurality of cells based on cellular phenotype using an imaging cell sorter, and a step of identifying the test target used to treat each cell using the first barcode nucleic acid as an indicator.

Definitions

In the present specification, "genome-related information" means information related to the cell genome or derivatives thereof and refers to information related to changes in nucleic acids and proteins accompanying changes in gene expression. In addition, here, "genome-related nucleic acid" is a nucleic acid related to genome-related information and suitable examples thereof are the genome DNAs of a cell, RNAs such as mRNAs derived from a cell genome, or cDNAs thereof. In addition, another example of a "genome-related nucleic acid" includes a nucleic acid probe which specifically interacts (for example, binds) with a molecule such as a protein expressed in a cell. In addition, in a case where the nucleic acid is genome DNA, the DNA may be a fragment cut with a restriction enzyme or the like, or a DNA tag may be introduced into the DNA fragment.

In the present specification, a "barcode region" is a region of the base sequence including T (thymine) or U (uracil), A (adenine), G (guanine), and C (cytosine) and is not limited beyond being the sequence of the common barcode region or the unique barcode region described below. In addition, a barcode nucleic acid is a nucleic acid including a barcode region, which enables the identification of genome-related information of a cell and imaging information derived from the test target or a bead coexisting with the cell.

Barcode regions include two types, which are common barcode regions and unique barcode regions.

The length of the barcode region is not limited; however, the sequence is preferably 8 to 40 bases long. For example, in a case where the barcode region is 12 bases long, it is possible to carry out nucleic acid amplification on $4^{12}$ types of diverse barcode sequences at one time.

A "common barcode region" is a barcode region common to the same objects for identification. In a case where the object for identification is a test target, examples thereof include a barcode region which is different for each test target, that is, a barcode region which is common to one test target. Tagging with a common barcode region makes it possible to identify each test target. In addition, in a case where the object for identification is a combination of test targets, such as where a combination of test targets are included in one compartment, tagging is carried out with a barcode nucleic acid which has a barcode region which is different for each combination, that is, a barcode region which is common to a specific combination of test targets. Tagging with such a common barcode region makes it possible to identify the combination of test targets. In a case where the object for identification is the genome-related information of a single cell, examples thereof include a barcode region which is different for each cell, that is, a barcode region which is common to a single cell. Tagging with the common barcode region makes it possible to identify genome-related information derived from the same cell.

A "unique barcode region" is a barcode region with which it is possible to distinguish each barcode nucleic acid individually by tagging each barcode nucleic acid with a different barcode region. For example, tagging in the unique barcode region makes it possible to identify the bead linked to each barcode nucleic acid, organisms including each barcode nucleic acid, and genome-related nucleic acids hybridized with each barcode nucleic acid.

In the present specification, "hybridize" signifies that the hybridization region of a barcode nucleic acid forms a double-stranded complex with a cell genome or derivative thereof or another barcode nucleic acid. Here, examples of exemplary conditions for forming such double-stranded complexes include hybridization at 37° C., 40% to 45% formamide, 1.0 M NaCl, 0.1% SDS, and washing in 0.5×-1× SSC at 55° C. to 60° C. Examples of other aspects when forming the double-stranded complexes described above include performing the complex formation under stringent conditions. Here, stringent conditions refer to the conditions under which so-called specific complexes are formed and non-specific complexes are not formed, including the exemplary conditions described above. Such stringent conditions are known to those skilled in the art and are able to be set with reference to, for example, in Molecular Cloning (Third Edition, Cold Spring Harbor Laboratory Press, New York) and Current protocols in molecular biology (edited by Frederick M. Ausubel et al., 1987). Examples of a sequence with which the hybridization region of the barcode nucleic acid is hybridized include a complementary sequence to the hybridization region.

Accordingly, the "hybridization region" is preferably a region which binds to (hybridizes with) a genome-related nucleic acid corresponding to a cell genome or a derivative thereof or another barcode nucleic acid. Such a hybridization region is preferably present with the barcode region in the barcode nucleic acid.

A description will be given below of one embodiment of the screening method of the present disclosure in accordance with FIG. 1.

In the method of the present disclosure, cells treated with test targets and tagged with first barcode nucleic acids are prepared. Such a preparing step may include, for example, the following steps (step 1-1 to step 1-3 in FIG. 1).

Step 1: A Step of Preparing a Plurality of Cells Tagged with First Barcode Nucleic Acids Associated with Test Targets and Treated with the Test Targets.

Step 1-1: Generating Sub-Compartments (Droplets) (a Step of Forming Droplets Including the Test Target and the First Barcode Nucleic Acid Corresponding to the Test Target.)

According to an embodiment of the present disclosure, as shown in the upper part of step 1-1 in FIG. 1, a liquid medium including a test target and a first barcode nucleic acid is mixed with an organic solvent to form a sub-compartment (droplet) including the test target and the first barcode nucleic acid corresponding to the test target. Specifically, for example, it is possible to add hydrogel beads to the liquid medium including the test target and the first barcode nucleic acid to generate the first sub-compartment including the test target and the first barcode nucleic acid. In a more specific method, it is possible to generate a large number of homogeneous droplets including the test target and the first barcode nucleic acid corresponding to the test target by mixing hydrogel particles prepared in advance with the test target and the first barcode nucleic acid corresponding to the test target and adding an organic solvent and surfactant thereto to carry out vortexing in each container (for example, each well). In addition, by the similar method, it is also possible to carry out the steps described above according to the method described in Anal. Chem., 2018, 90, 16, 9813-9820. For example, it is possible to use beads made of materials such as acrylamide, agarose, collagen, alginate, or polyethylene glycol, as the hydrogel particles added as templates in this step.

The test targets of the present disclosure are not particularly limited as long as they are test targets for which a desired response in a cell is to be studied and examples thereof include test substances such as low molecular weight organic compounds, peptide compounds, nucleic acid compounds having nucleic acids or derivatives thereof as a basic framework, polypeptides or proteins such as enzymes, antibodies, and antibody fragments, cells, viruses, and drugs.

The types of cells to be studied are not particularly limited as long as the effects of the present disclosure are not interfered with and it is possible to select cells according to the purpose, for example, it is possible to use human-derived cells such as patient blood cell-derived cells or cells induced differentiation into target cells from stem cells such as iPS cells (induced pluripotent stem cells) and mammalian-derived cells such as CHO (Chinese Hamster Ovary) cells.

Step 1-2: Generation of Compartments by Fusion of Sub-Compartments (a Step of Fusing a Sub-Compartment (Droplet) Including a Test Target and a First Barcode Nucleic Acid Corresponding to the Test Target and a Sub-Compartment (Droplet) Including a Cell)

In addition, according to an embodiment of the present disclosure, as shown in step 1-2, a step is carried out in which a droplet including the test target and the first barcode nucleic acid and a droplet including the cell are mixed to associate the test target, the first barcode nucleic acid, and the cell. Specifically, the association of the test target, the first barcode nucleic acid, and the cell may be carried out by fusing the first sub-compartment including the test target and the first barcode nucleic acid and the second sub-compartment including the cell and generating a compartment including the test target, the first barcode nucleic acid, and the cell. In a more specific method, in a microfluidic device, by pouring a group of droplets including the test target and the first barcode nucleic acid corresponding to the test target from one channel and a group of droplets including cells from another channel and carrying out sequential droplet-to-droplet fusion in the microfluidic device, it is possible to generate a large number of droplets including the cell, the test target, and the first barcode nucleic acid corresponding to the test target in the organic solvent phase. At this time, as in the example described below, by forming a droplet including the cell in the microfluidic device and fusing the droplets with droplets including the test target and the first barcode nucleic acid corresponding to the test target, it is also possible to generate a droplet including the cell, the test target, and the first barcode nucleic acid corresponding to the test target. In the droplet in the organic solvent phase described above, it is possible to tag the cell with the first barcode nucleic acid by attaching the barcode nucleic acid corresponding to the test target to the cell surface while the cells are affected by the test target. It is possible to carry out the step described above according to the method described in Anal. Chem. 2018, 90, 2, 1273-1279.

A compartment or sub-compartment is a unit of compartmentation which makes it possible to distinguish each combination of components in the compartment or sub-compartment from other compartments.

The type and number of test targets included in the compartments in the present disclosure are not particularly limited as long as the effects of the present disclosure are not interfered with, but from the viewpoint of simplifying or clarifying the cellular response, one type per compartment is preferable. However, for example, in a case where a plurality of test targets are combined to examine the response of cells to the test targets, the number of test target types per compartment may be plural. In addition, the concentration of the test target may be set to be different in each, which makes it possible to evaluate the cellular response at different concentrations of the test target. Such aspects are also encompassed in the present disclosure.

The compartments of the present disclosure are not particularly limited as long as it is possible to maintain compartments which are able to be distinguished from other compartments and examples thereof include aqueous droplets (for example, aqueous droplets in oil) generated by the step described above. Further examples thereof include gel particles of hydrogels, water/oil structures with a plurality of overlapping unmixed interfaces such as emulsions, vesicles with monolayers or bilayers such as micelles or liposomes, and the like. At this time, for the aqueous phase included in the droplet, for example, it is possible to use an aqueous solution such as a cell culture medium, physiological saline, or a buffer solution. In addition, for the organic solvent phase, for example, it is possible to use an oil such as Droplet Generator oil for EvaGreen (manufactured by Bio-Rad Laboratories, Inc.).

The compartment of the present disclosure preferably has a physical barrier function at the periphery thereof from the viewpoint of being distinguished from other compartments. Examples of a suitable method for generating a compartment having such a barrier function include a phase separation method or the like. In the phase separation method, for example, it is possible to generate compartments by mixing cells and beads with an aqueous substrate to obtain aqueous droplets and then suspending the aqueous droplets in a hydrophobic solvent. In addition, it is also possible to generate compartments by mixing droplets together at a branch portion or merging portion in a microfluidic device.

In addition, it is also possible to form the compartments of the present disclosure by encompassing the compartments in a container such as a microwell, well, or tube. In such a case, the association, that is, the contact, of the test target and the first barcode corresponding to the test target with the cells occurs by the coexistence in the well or the like.

In addition, according to an embodiment of the present disclosure, it is possible to tag cells with the first barcode nucleic acid in a compartment including the test target, the first barcode nucleic acid, and the cells. It is desirable for the first barcode nucleic acid to have a configuration including an anchor able to link the first barcode nucleic acid to the cell surface (for example, a known anchor provided with an oligonucleotide region and a lipid region (cholesterol, chitosan-glycol-lipid, or the like)). In particular, preferable examples thereof include anchor DNA and the like, which are used in examples described below. In addition, the first barcode nucleic acid may also be used in a form which is encompassed in or bound to a particle or the like. In such a case, the first barcode nucleic acid is designed to be released from the encompassing particle or the like as appropriate.

A description will be given below in details about the configuration of the first barcode nucleic acid.

In addition, according to one embodiment of the present disclosure, it is possible to carry out the treatment of the cells by a test target in a compartment.

As necessary, culturing may be carried out in a state where the cells and the test target coexist in the compartment. Examples of such culturing include holding the compartment for a desired culture time at a desired culture temperature. In holding the compartments, the compartments may be moved and held in a reservoir able to hold a plurality of compartments. It is possible to carry out the step described above using known methods. For example, it is possible to perform the above according to the methods described in J. J. Agresti et al, Proc Natl Acad Sci USA., 107(9), 4004-9 (2010), A. Abbaspourrad et al, Sci Rep., 5, 12756 (2015), B. L. Wang et al., Nat Biotechnol. 32(5), 473-8 (2014).

Here, as the culture time and culture temperature, it is possible to set the culture time and culture temperature to a level which enables evaluation of the response of the cells with respect to the test target. Examples of the culture time include 0 hours or more and 14 days or less, and preferably 2 hours or more and 5 days or less. Examples of the culture temperature include 4° C. or higher and 40° C. or lower, and preferably a temperature around 37° C.

One embodiment of the search for a test target of the present disclosure includes a search for a target site in which a desired phenotypic change occurs in a cell, in addition to a search for a test target which causes a phenotypic change in a cell as described above. The search for the target site includes, for example, searching for a target position (target) on the gene where the desired phenotypic change occurs. By tagging the cells with a first barcode nucleic acid which specifies information which specifies the procedure to be applied to the cells in advance (for example, information which specifies the position at which gene editing occurs, information regarding the nucleic acid sequence of guide RNA or the like used for gene editing, or the like), it is possible to add information which specifies the treatment carried out on the cells to the cells classified and acquired by the imaging cell sorter, thus, it is possible to efficiently perform the search for the target position (target) on the gene where the desired phenotypic change occurs, using the imaging cell sorter.

Step 1-3: Disruption of Compartments (Step of Recovering Cells Tagged with First Barcode Nucleic Acid)

An embodiment of the present disclosure includes a step of recovering cells from the compartment described above, as shown in step 1-3 of FIG. 1. As a specific method, it is possible to recover cells tagged with the first barcode nucleic acid from droplets in the organic solvent phase (including cells affected by the test target and tagged with the first barcode nucleic acid). In the recovering step described above, it is possible to carry out the above, for example, by adding an organic solvent to the organic solvent phase to cause phase separation, or by applying an electric field to the organic solvent phase.

Since the recovered cells are tagged with the first barcode nucleic acid associated with the test target, even if a plurality of cells treated by different test targets are mixed together, it is possible to identify the information relating to the test target through a step of reading nucleic acid information described below. Accordingly, by mixing a plurality of cells tagged with the first barcode nucleic acid recovered by this step and further separating the cells generating a predetermined phenotype by image-based cell sorting described below, for the cells in which a desired cellular phenotypic change occurs, it is possible to simultaneously obtain genome-related information in that specific cell and information on the treated test target.

Step 2: Cell Sorting (Image-Based Cell Sorting)

According to an embodiment of the present disclosure, a step of sorting a plurality of cells based on cellular phenotype is carried out using an imaging cell sorter, as shown in step 2 of FIG. 1. According to a preferable embodiment of the present disclosure, it is possible to sort cells in which a predetermined reaction is occurring due to the test target based on the cellular phenotype. A description will be given below of more specific aspects of the imaging cell sorter, but examples of the imaging cell sorter include the apparatuses described in WO2017/073737 and WO2018/181458. In the imaging cell sorter described in the documents described above, it is possible to carry out sorting quickly and accurately by carrying out analysis based on signals such as lights and electromagnetic waves from the cells which are the observation object without obtaining photographic images, optimizing the light source system or detection system by machine learning, and also optimizing the method for analyzing and classifying the observation objects by machine learning.

Step 3: Identification of the Test Targets which Cause Desired Cellular Change (Nucleic Acid Information Reading)

According to an embodiment of the present disclosure, as shown in step 3 of FIG. 1, a step of identifying the test target used for treating each cell with the first barcode nucleic acid as an indicator is carried out. In this step, it is possible to read the nucleic acid information of the first barcode nucleic acid and associate the change in cellular phenotype with the test target, thus making it possible to identify the test target which cause a desired cellular phenotypic change.

Furthermore, in the present disclosure, the genome-related information of each cell sorted by phenotype using an imaging cell sorter is preferably analyzed. By analyzing the genome-related information of each cell, it is possible to make an association with the relationship of the cellular phenotypic change, the genome-related information of the cell, and the test target. Therefore, it is possible to obtain additional information relating to the phenomenon occurring in the cell in which the desired phenotypic change occurred due to the test target at the genetic level, which means making more detailed information relating to the phenomenon available.

As an example, a description will be given below of a step of analyzing the preferable nucleic acid information of the present disclosure. Here, the nucleic acid information includes the information of the first barcode nucleic acid associated with the test target and the nucleic acid information of the genome-related nucleic acid corresponding to the cell-derived genome or derivatives thereof.

According to an embodiment of the present disclosure, the step of analyzing nucleic acid information described above includes a step of preparing a plurality of compartments including a cell exhibiting a desired phenotypic change which is sorted using an imaging cell sorter, a first barcode nucleic acid, and a second barcode nucleic acid linking bead which includes a plurality of second barcode nucleic acids hybridizable with the genome-related nucleic acid corresponding to the cell genome or derivatives thereof or the first barcode nucleic acid, a step of obtaining a hybridized complexes by hybridizing each of the genome-related nucleic acid and the first barcode nucleic acid with the second barcode nucleic acid, a step of producing amplified products derived from the hybridized complexes described above, and a step of detecting genome-related information after the coexistence of the first barcode nucleic acid and the test target with the cell, using an expression pattern of the amplified products described above as an indicator.

A description will be given below of an embodiment of a step of analyzing nucleic acid information, based on FIG. 2.

A large number of droplets (compartments) are generated in a micro flow path and, preferably, mixed such that, in each droplet, a second barcode nucleic acid linking bead which is different for each droplet and a cell exhibiting the desired phenotypic change are probabilistically included in a ratio of 1:1. The cells are then lysed within the compartment described above, and genome-related nucleic acids corresponding to the cell genome or derivatives thereof and the first barcode nucleic acid used as a tag for the test target are encompassed in the compartment in a state of being hybridized with the second barcode nucleic acid linking bead, as shown in the upper left part of FIG. 2.

First Barcode Nucleic Acid

The first barcode nucleic acid of the present disclosure is not limited as long as a barcode region corresponding to each test target is included therein and, for example, the nucleic acid is RNA, DNA, or a combination thereof.

Figure 2:
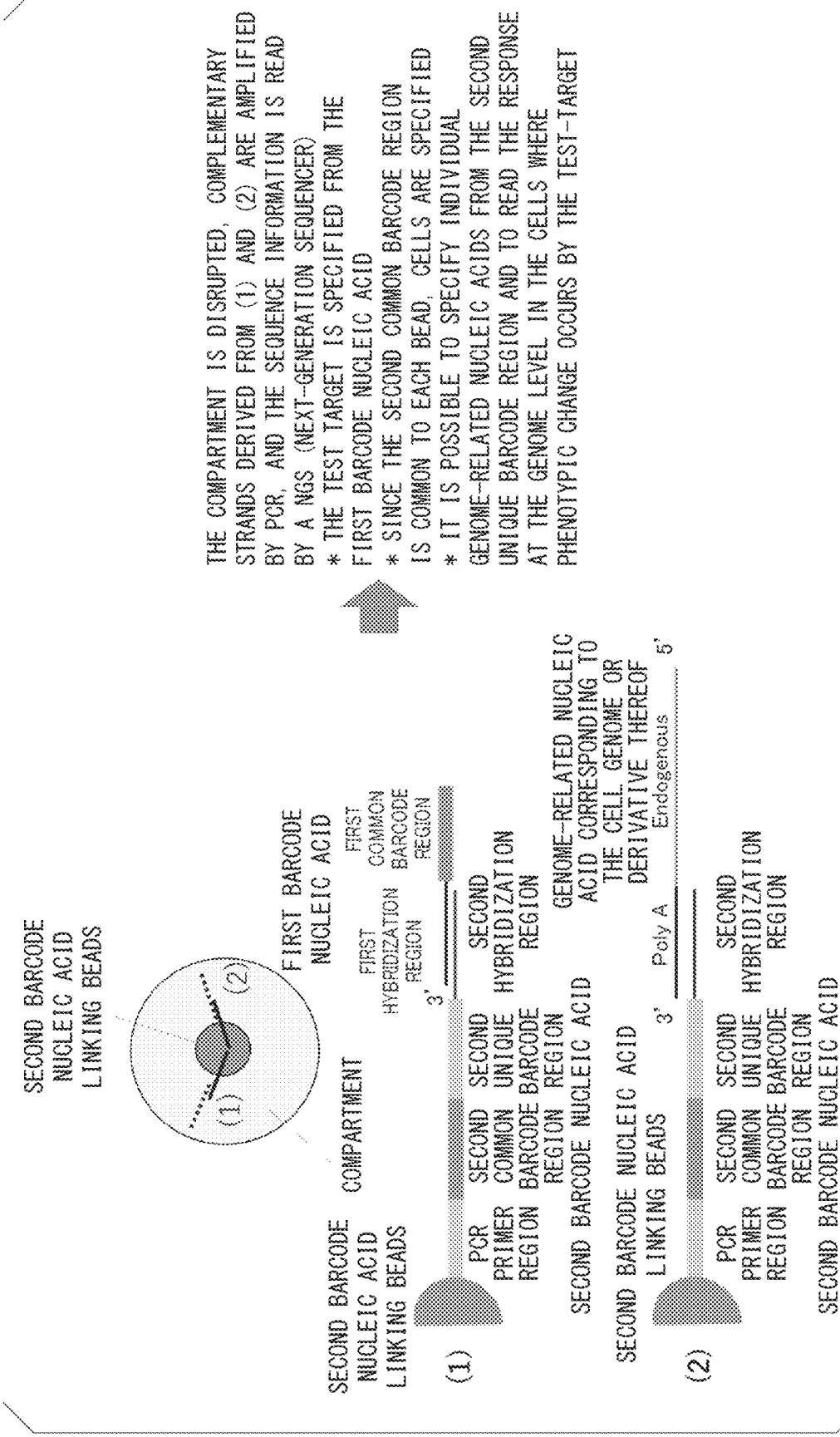
FIG. 2 is a conceptual diagram for illustrating an embodiment of a step of reading nucleic acid information of each cell in the screening method of the present disclosure. (1) shows hybridization of a second barcode nucleic acid with a first barcode nucleic acid, and (2) shows hybridization of the second barcode nucleic acid with the cell genome or the genome-related nucleic acid corresponding to a derivative thereof.

As shown in (1) of FIG. 2, according to an embodiment of the present disclosure, the first barcode nucleic acid preferably includes a first common barcode region corresponding to each test target and a first hybridization region hybridizable with the second barcode nucleic acid. For example, the first hybridization region is a sequence formed of polyadenine and this portion hybridizable with the second hybridization region (for example, a sequence formed of polythiamine) of the second barcode nucleic acid linking bead. Here, using the sequence information of the first common barcode region makes it possible to identify the same test target in a one-to-one correspondence. Accordingly, using the sequence information of the first common barcode region makes it possible to identify the test target present in the compartment.

For the first barcode nucleic acid, a specific nucleic acid sequence is generated by a solid phase synthesis method or an enzymatic synthesis method. In a case where the barcode nucleic acid is an RNA, after synthesizing a DNA template that serves as the complementary strand of the single-stranded barcode nucleic acid, an RNA may be synthesized by an RNA polymerase such as T7, which binds to the promoter sequence on the DNA template and synthesizes the RNA including the single-stranded barcode region by a linear amplification reaction. In a case where the barcode nucleic acid is a DNA, the barcode nucleic acid is not particularly limited as long as the effects of the present disclosure are not interfered with and may, for example, be synthesized and/or designed using known sequences.

Second Barcode Nucleic Acid Linking Bead

As shown in (1) and (2) in FIG. 2, the second barcode nucleic acid linking bead is linked to second barcode nucleic acids which include hybridizable sequences with a genome-related nucleic acid corresponding to the cell genome or derivatives thereof or the first barcode nucleic acid.

The number of the second barcode nucleic acid linking beads described above per compartment is not particularly limited, but one per compartment is preferable.

Second Barcode Nucleic Acid

In addition, the lower parts of (1) and (2) in FIG. 2 are magnified views of the surface of the second barcode nucleic acid linking bead and show examples of the structure of the second barcode nucleic acid linked to the bead.

The second barcode nucleic acid may be directly or indirectly linked to the second bead. According to an embodiment of the present disclosure, the second barcode nucleic acid is RNA, DNA, or a combination thereof.

According to an embodiment of the present disclosure, as also shown in the lower parts of (1) and (2) in FIG. 2, the second barcode nucleic acids preferably include second common barcode regions common to each other among a plurality of second barcode nucleic acids linked to a bead, second unique barcode regions which are able to be distinguished from each other among a plurality of second barcode nucleic acids linked to the bead, and second hybridization regions hybridizable with the genome-related nucleic acid or the first barcode nucleic acid. In addition, the second barcode nucleic acids preferably also include a PCR primer region. In one example of the lower parts of (1) and (2) in FIG. 2, a second barcode nucleic acid includes, in order from the bead side, a PCR primer region, a second common barcode region, a second unique barcode region, and a second hybridization region.

As shown in (2) of FIG. 2, as described above, the sequence information of the second common barcode region described above is common to each other among the plurality of second barcode nucleic acids which are linked to a bead and is able to be used as an indicator for specifying the cell from which the genome-related nucleic acid is derived, due to being associated with the cell-derived genome-related nucleic acids by hybridization. Furthermore, since cells are sorted by phenotype using an imaging cell sorter, the sequence information of the second common barcode region is associated with the phenotype (imaging information) of the cell and is also able to be used as an indicator of the phenotype of the cell.

In addition, since the sequence information of the second unique barcode region described above makes it possible to distinguish each second barcode nucleic acid from others while genome-related nucleic acids which are individually hybridized with a second barcode nucleic acid is able to be specified, it is possible to analyze reactions at the genome level, such as which amounts of genome-related nucleic acids expression increased in the cells in which phenotypic changes occurred.

As shown in (1) of FIG. 2, the second hybridization region of the second barcode nucleic acid is also hybridizable with a first barcode nucleic acid, thus, the sequence information such as the first common barcode region of the first barcode nucleic acid associated with the test target is also able to be associated with the sequence information of the second barcode nucleic acid described above. According to a preferable embodiment, the second hybridization region of a second barcode nucleic acid includes a nucleic acid which is complementary to the first hybridization region or genome-related nucleic acids.

For example, in a case where the genome-related nucleic acid is an mRNA, the second hybridization region in the second barcode nucleic acid is preferably a polythymine composed of T. It is sufficient if the length of the polythymine is long enough to be able to anneal to (hybridize with) the polyadenine (A) tail of the mRNA.

In a case where the genome-related nucleic acid is DNA, such as genome DNA, the second hybridization region in the second barcode nucleic acid preferably includes a sequence which is complementary to a specific sequence of the DNA or a sequence of a DNA tag introduced into the DNA.

As a whole second barcode nucleic acid, each second barcode nucleic acid can have a different sequence from each other. The plurality of second barcode nucleic acids linked to a bead are preferably a plurality of types of second barcode nucleic acids.

Beads

From the viewpoint of being able to hybridize with a large number of genome-related nucleic acids, it is preferable that 1,000 to 100,000 second barcode nucleic acids are linked to a bead.

In a case where the beads are particles, the material thereof is not particularly limited and examples thereof include semiconductors such as quantum dots (semiconductor nanoparticles) made of semiconductor materials such as cadmium selenide (CdSe), zinc sulfide (ZnS), cadmium sulfide (CdS), zinc selenide (ZnSe), zinc oxide (ZnO), and silicon dioxide ($SiO_2$), inorganic materials such as heavy metals such as gold, hydrogels such as acrylamide, agarose, collagen, alginate, cellulose, chitosan, hyaluronic acid, silicone hydrogels, PEG-based hydrogels or the like, resins such as polystyrene, polypropylene, hydrophilic vinyl polymers (such as Toyopearl HW-65S (Tosoh Corporation)) or the like, or these hydrogel materials which are chemically cross-linked, or hydrophilic vinyl polymers to which PEG or derivatives thereof are bound, or the like, preferable examples include hydrogels, and more preferable examples include acrylamide and alginate.

Method for Generating Second Barcode Nucleic Acid Linking Beads

It is possible to generate a plurality of types of second barcode nucleic acid linking beads by known methods. For example, it is possible to generate the second barcode nucleic acid linking beads according to the methods described in E. Z. Macosko et al, Highly Parallel Genome-wide Expression Profiling of Individual Cells Using Nanoliter Droplets. Cell. 161, 1202-1214 (2015) or Gierahn, T. M et al., Seq-Well: A Portable, Low-Cost Platform for High Throughput Single-Cell RNA-Seq of Low-Input Samples; Nat Methods. 14, 395-398 (2017).

Cells or Derivatives Thereof

Genome-related nucleic acids corresponding to cell genomes or derivatives thereof to be enclosed in the compartments described above include nucleic acids obtained from cell fractures, cell contents, cell lysates, and the like. It is possible to acquire cell derivatives (for example, cell fractures, contents, lysates, or the like) using known techniques such as placing cells and a cell lysis buffer or the like into coexistence.

The step of acquiring genome-related nucleic acids corresponding to the cell genome or derivatives thereof may be performed by enclosing cells tagged with the first barcode nucleic acid together with a cell lysis buffer or the like when generating the compartment, or by enclosing a cell lysis buffer together with cells tagged with the first barcode nucleic acid and the second barcode nucleic acid linking beads to generate the above in the compartment. At this time, the number of cells enclosed in the compartment is not limited as long as the effects of the present disclosure are not interfered with, but from the viewpoint of single cell analysis, one cell per a compartment is preferable.

Step of Acquiring Hybridized Complex

In addition, according to an embodiment of the present disclosure, in the step of analyzing genome-related information described above, a step of hybridizing each of the genome-related nucleic acid and the first barcode nucleic acid with the second barcode nucleic acid to obtain a hybridized complex, is carried out.

It is possible to perform the step described above by known methods. For example, it is possible to perform the step according to the methods described in E. Z. Macosko et al, Highly Parallel Genome-wide Expression Profiling of Individual Cells Using Nanoliter Droplets. Cell. 161, 1202-1214 (2015), or Zheng G X et al., Massively parallel digital transcriptional profiling of single cells. Nat Commun. 6; 8: 14049 (2017). Subsequently, the compartment may be disrupted by a known method.

Step of Making an Amplified Product Derived from a Hybridized Complex

In addition, according to an embodiment of the present disclosure, in the step of analyzing genome-related information described above, a step of making an amplified product derived from a hybridized complex obtained in the hybridized complex acquiring step described above is carried out.

It is possible to perform the step described above by a known method. For example, it is possible to perform the step according to the methods described in E. Z. Macosko et al, Highly Parallel Genome-wide Expression Profiling of Individual Cells Using Nanoliter Droplets. Cell. 161, 1202-1214 (2015), or Zheng G X et al., Massively parallel digital transcriptional profiling of single cells. Nat Commun. 6; 8: 14049 (2017).

According to one specific embodiment, synthesis of complementary strand DNA and a reverse transcription reaction are performed with respect to a hybridized complex obtained in the hybridized complex acquiring step described above. By the synthesis and reverse transcription reaction, cDNAs with respect to cell-derived mRNAs and complementary strand DNAs with respect to the first barcode nucleic acid are synthesized. Subsequently, template switching may be performed.

Subsequently, a PCR reaction is preferably performed. Two types of amplified products, which are a first amplified product derived from a hybridized complex of the first barcode nucleic acid and the second barcode nucleic acid and a second amplified product derived from a hybridized complex of the cell-derived mRNA and the second barcode nucleic acid can be generated by this PCR reaction. In a case where the genome-related nucleic acid is DNA, it is possible to perform the extension PCR method as the PCR reaction described above. Subsequently, based on the obtained amplified products, it is possible to generate a library of amplified products, including the first amplified product and second amplified product, derived from the treatment of the test target.

Step of Reading Nucleic Acid Information after Coexistence of Test Target with Cells In addition, according to an embodiment of the present disclosure, there is included a step of identifying a test target coexisting with cells and detecting genome-related information of the cells, using the expression pattern of the amplified products obtained in the step of making the amplified product derived from the hybridized complex described above as an indicator. Examples of the expression pattern of the amplified products described above include sequence information of the amplified products obtained by sequencing, for example, sequence information of the first barcode nucleic acid in the sequence information (for example, sequence information of the first common barcode region), sequence information of the second barcode nucleic acid (for example, sequence information of the second common barcode region, sequence information of the second unique barcode region), sequence information of the genome-related nucleic acid (sequence of mRNA for each cell), and the like.

Without being particularly limited thereto, a description will be given below of an aspect of the step of reading nucleic acid information after coexistence of a test target with cells.

The sequences of the amplified products (first amplified product and second amplified product) obtained in the step of making an amplified product derived from the hybridized complex described above are determined by a sequencer and analysis of the sequence information of the amplified products is performed. In the analysis of the second amplified product, the cells from which each amplified product is derived are assigned using the sequence information of the second common barcode region as an indicator. In addition, since it is possible to identify each mRNA molecule separately by the sequence information of the second unique barcode region, it becomes possible to obtain information such as the sequence of mRNAs and their expression amount for each cell using the sequence information as an indicator. Based on the information obtained by the analysis of the second amplified products described above, it is possible to obtain transcriptome information for each cell.

Next, identification of the test target coexisting with the cells described above is performed. Here, as described above, the first barcode nucleic acid corresponds to the test target. Accordingly, in the identification described above, based on the sequence information of the first common barcode region of the first barcode nucleic acid, the test target coexisting with the cells can be assigned to each first amplified product.

Next, matching of the test target coexisting with the cells with the transcriptome information is performed. Accordingly, it is possible to associate the genome-related information of the cell in each compartment with the test targets coexisting therewith on a one-to-one basis.

Accordingly, by detecting genome-related information such as transcriptome information of the cells or derivatives thereof coexisting with one or more types of test targets, it is possible to evaluate the response of the cells with respect to the test targets coexisting therewith.

It is possible to carry out the step of reading nucleic acid information described above using, for example, a Chromium Controller apparatus and a Single Cell 3' Reagent Kits v3 manufactured by 10× Genomics, which is a single cell analysis technology using a droplet technique.

Imaging Cell Sorter

In the present disclosure, as described above, a plurality of cells are sorted based on their cellular phenotype using an imaging cell sorter. In the present disclosure, using the imaging cell sorter makes it possible to rapidly and accurately analyze cellular phenotypic changes occurring in response to a test target and to sort the cells which exhibit the desired phenotype. The imaging cell sorter is a flow cytometer which rapidly acquires and analyzes morphological information of an observation object such as a cell and which is able to selectively acquire the desired observation object based on the analysis results.

Imaging Cell Sorter of First Embodiment

According to an embodiment of the present disclosure, an imaging cell sorter is an analysis apparatus provided with an analysis unit. The analysis unit analyzes an observation object based on a signal extracted in time sequence from electrical signals output from a light receiving unit. The light receiving unit receives scattered light, transmitted light, fluorescent light, or electromagnetic waves from the observation object present in a light-irradiated region where the structured light from a light source is irradiated and converts them to electrical signals. Hereinafter, the imaging cell sorter of the present embodiment is also referred to as an "imaging cell sorter in the first embodiment". The imaging cell sorter in the first embodiment uses a dynamic ghost imaging (Ghost Motion Imaging) technique which uses relative motion of the optical structure and the observation object. It is possible to carry out the analysis using the imaging cell sorter in the first embodiment according to the description in WO2017/073737, for example.

According to the imaging cell sorter in the first embodiment of the present disclosure, delegating each key point of the single-cell flow cytometry to machine learning makes it possible to measure cellular information intelligently and analyze and classify cellular information intelligently, quickly, and accurately. It is possible to realize (1) a cell classification method which is not limited by human knowledge bias, (2) a high-speed imaging/analyzing method of cell spatial information without obtaining cell's "photographic images", and (3) an optical capturing method which is automatically optimized according to the object.

Figure 3:
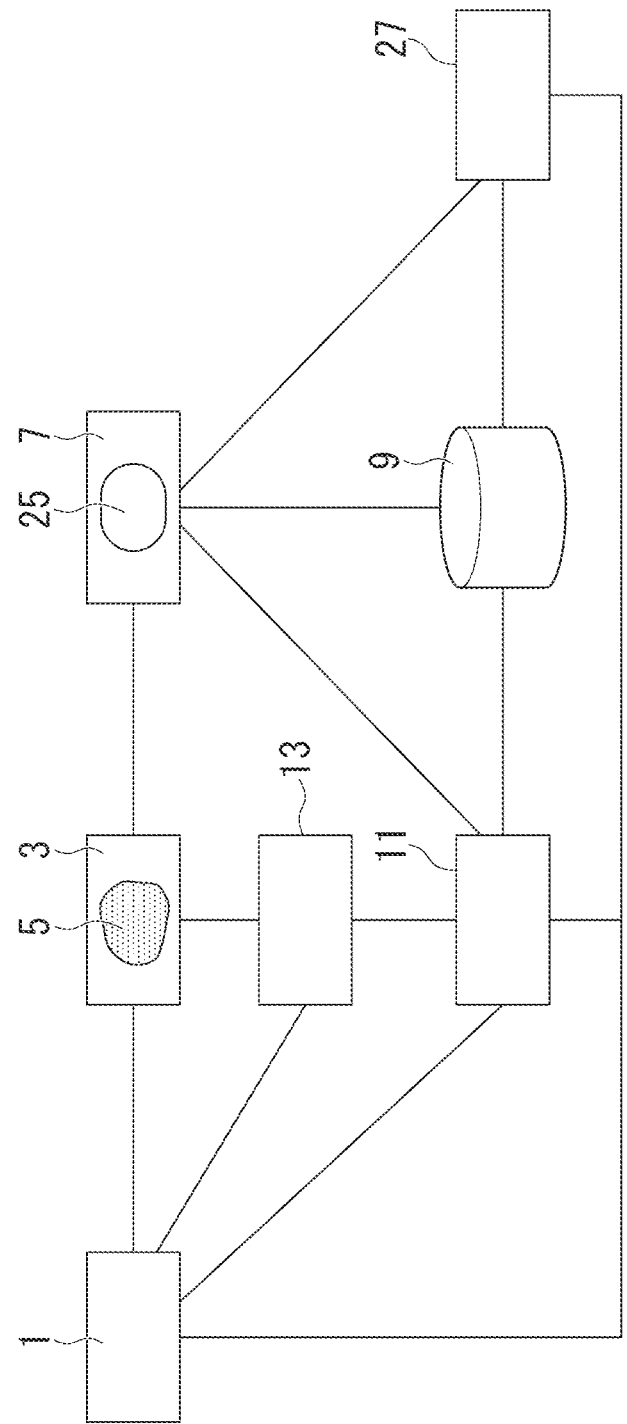
FIG. 3 is a schematic diagram showing an embodiment of an imaging cell sorter in the first embodiment of the present disclosure.

FIG. 3 is a schematic diagram showing an embodiment of an imaging cell sorter in the first embodiment of the present disclosure. As an example, the imaging cell sorter in the first embodiment of the present disclosure has a light source 1, a light-irradiated region 3 irradiated with light from the light source 1, a light receiving unit 7 which receives scattered light (including Raman scattering), transmitted light, fluorescent light, or electromagnetic waves from an observation object 5 present in the light-irradiated region 3 and converts the light or the electromagnetic waves into electrical signals, a storage unit 9 which receives electrical signals from the light receiving unit 7 and records the electrical signals, an analysis unit 11 which analyzes the electrical signals relating to the scattered light, transmitted light, fluorescent light, or electromagnetic waves which are recorded by the storage unit 9 and records the analysis results, and an optical system control unit 13 which optimizes the light source 1 or the light-irradiated region 3 based on the analysis results.

In the imaging cell sorter in the first embodiment of the present disclosure, the light irradiated in the light-irradiated region 3 has a structured illumination pattern. As an example, a structured illumination pattern is provided by an optical modulation unit including a spatial light modulator, a filter, and the like, arranged in the middle of the optical path from the light source 1 to the light-irradiated region 3. Here, structured illumination is illumination having a plurality of regions with different optical characteristics, and the illumination light irradiating the observation object in the light-irradiated region 3 is modulated, for example, into a cingulate light in which a plurality of regions having different optical characteristics from each other are arranged in a grid-like manner and the plurality of regions comprise at least regions having a first optical characteristic and regions having a second optical characteristic. It is also possible to configure the imaging cell sorter in the first embodiment of the present disclosure not to include the optical system control unit 13 from the configuration of FIG. 3 described above.

In addition, as another embodiment of the imaging cell sorter in the first embodiment, it is also possible to have a configuration in which scattered light (including Raman scattering), transmitted light, fluorescent light, or electromagnetic waves from the observation object 5 are structured before detected by the light receiving unit 7, without structuring the light irradiated in the light-irradiated region 3. In this configuration, as an example, by arranging an optical modulation unit such as a filter in the middle of the optical path from the light-irradiated region 3 to the light receiving unit 7, it is possible to structure and detect light from the observation object 5 (scattered light, transmitted light, fluorescent light, or electromagnetic waves from the observation object 5 described above). As an example, the optical modulation unit used in the structured detection configuration has a plurality of regions arranged in a grid-like manner, and the plurality of regions has a pattern by the arrangement of regions which transmit light and regions which do not transmit light. Light from the observation object 5 goes through the optical modulation unit described above. Then, the light having a plurality of regions with different optical characteristics is detected by the light receiving unit 7.

The imaging cell sorter in the first embodiment of the present disclosure preferably optimizes the classification algorithm of the analysis unit 11 by machine learning. In the imaging cell sorter in the first embodiment of the present disclosure, it is possible to acquire training data using a training sample including cells exhibiting a desired phenotype, to generate a classification model which classifies cells exhibiting the desired phenotype using the training data, to measure a test sample, and to acquire cells exhibiting the desired phenotype from the test sample based on the model.

In the imaging cell sorter in the first embodiment of the present disclosure, preferably, the analysis unit 11 analyzes an observation object without reconstructing the image of the observation object from electrical signals related to scattered light, transmitted light, fluorescent light, or electromagnetic waves. That is, the electrical signals relating to the scattered light, transmitted light, fluorescent light, or electromagnetic waves are used as time-series waveform data in the analysis. The imaging cell sorter in the first embodiment of the present disclosure more preferably acquires waveform data (electrical signals) acquired using a training sample including cells exhibiting the desired phenotype as training data and generates a classification model which is used to classify cells exhibiting the desired phenotype using the training data. Then, more preferably in the imaging cell sorter in the first embodiment of the present disclosure, in the dependence upon the model, the cells exhibiting the desired phenotype are acquired from the test sample based on the waveform data (electrical signals) acquired when the test sample is measured.

In the imaging cell sorter in the first embodiment of the present disclosure, preferably, the optical system control unit 13 optimizes the light source 1 by machine learning.

In the imaging cell sorter in the first embodiment of the present disclosure, preferably, light from the light source 1 has a plurality of optical regions 21 and the optical system control unit 13 controls the optical structure of the plurality of optical regions. Accordingly, preferably, the imaging cell sorter in the first embodiment of the present disclosure has a plurality of optical regions and the optical system control unit controls the optical structure of the optical regions. In addition, according to an embodiment, in the imaging cell sorter in the first embodiment of the present disclosure, an optical modulation unit having a plurality of regions with different optical characteristics from each other is arranged on an optical path between the light source and the light-irradiated region. The light from the light source 1 is structured through the optical modulation unit and the observation object 5 is irradiated with the structured illumination in the light-irradiated region 3.

In the imaging cell sorter in the first embodiment of the present disclosure, preferably, the optical system control unit 13 analyzes the region where the observation object 3 is present based on electrical signals and controls and limits the light-irradiated region 3.

In the imaging cell sorter in the first embodiment of the present disclosure, preferably, the optical system control unit 13 analyzes the roughness of the observation object 5 based on the electrical signals to obtain the roughness information of the observation object and controls the light source 1 or the light-irradiated region 3 based on the roughness information. Accordingly, according to one embodiment, the analysis unit updates the classification algorithm based on the analysis results. In the imaging cell sorter in the first embodiment of the present disclosure, preferably, the light and the light-irradiated region are controlled based on the results analyzed by the analysis unit.

The imaging cell sorter in the first embodiment of the present disclosure preferably further has a light receiving system control unit 27 which receives electrical signals from the light receiving unit 7 and optimizes a light receiving region 25, which is the region where the light receiving unit 7 is irradiated with light. In the imaging cell sorter in the first embodiment of the present disclosure, the light receiving system control unit 27 preferably optimizes the light receiving region 25 by machine learning.

In a preferable use form, the imaging cell sorter in the first embodiment of the present disclosure has a flow cell including the light-irradiated region 3. The observation object 5 moves with the fluid flowing through the flow cell and is irradiated with light from the light source 1 in the light-irradiated region 3.

The imaging cell sorter in the first embodiment of the present disclosure preferably has a sorting unit which sorts the classified observation objects 5 based on the analysis results of the analysis unit 11.

Second Embodiment of Imaging Cell Sorter

In addition, according to a preferable embodiment of the present disclosure, an imaging cell sorter is an analysis apparatus provided with an analysis unit. The analysis unit analyzes an observation object based on a signal extracted in time sequence from electrical signals output from a light receiving unit. The light receiving unit receives scattered light, transmitted light, fluorescent light, or electromagnetic waves from the observation object present in a light-irradiated region where the light from a light source is irradiated and converts them to electrical signals. Hereinafter, the imaging cell sorter of the present embodiment is also referred to as an "imaging cell sorter in the second embodiment". It is possible to carry out the analysis using the imaging cell sorter in the second embodiment according to the description in WO2018/199080.

According to the imaging cell sorter in the second embodiment, it is possible to generate a three-dimensional image of the observation objects at high speed, which is advantageous in rapidly specifying the phenotype of the cells which are the observation objects.

The imaging cell sorter in the second embodiment is preferably an imaging flow cytometer provided with at least one flow path through which an observation object flows, a light source which irradiates the flow path with a cingulate excitation light, an imaging unit which obtains photographic images of a certain cross-section of the observation object by obtaining fluorescence from the observation object which passed through the position irradiated with the excitation light, and a three-dimensional image generating unit which generates a three-dimensional photographic image of the observation object based on a plurality of photographic images of cross-sections obtained by the imaging unit.

In addition, in the imaging cell sorter in the second embodiment, preferably, the observation object is sorted based on information indicating the morphology of the observation object shown in the cross-sectional photographic images obtained by the imaging unit.

In addition, in the imaging cell sorter in the second embodiment, preferably, the flow path is a plurality of flow paths lined up in parallel, the plurality of the flow paths are irradiated with the excitation light, and the imaging unit obtains cross-sectional photographic images of the observation objects flowing through each of the plurality of flow paths.

In addition, in the imaging cell sorter in the second embodiment, preferably, an optical modulation unit, which has a plurality of regions with different optical characteristics from each other, is arranged on an optical path between the light source and an image sensor which detects the intensity of the fluorescence and the imaging unit reconstructs an image of the cross-section of the observation object as a captured photographical image, based on the intensity of the fluorescence detected by the image sensor and the optical characteristics of the optical modulation unit.

According to the present disclosure, it is possible to provide an imaging flow cytometer which rapidly generates a three-dimensional image of an observation object.

According to one aspect, the method of the present disclosure may be carried out according to the methods described in the following Examples after the preparing step described above.

In addition, the contents described in Japanese Patent No. 5441142, Japanese Patent No. 5540359, Japanese Patent No. 6544600, WO2017/073737, WO2018/181458, WO2018/199080, and WO2018/203575 are a part of the present specification by reference.

According to an embodiment of the present disclosure, the following is provided.

[1] A method for screening a test target, the method including a step of preparing a plurality of cells which are tagged with a first barcode nucleic acid associated with a test target and treated with the test target, a step of sorting the plurality of cells based on cellular phenotype using an imaging cell sorter, and a step of identifying the test target used to treat each cell using the first barcode nucleic acid as an indicator.

[2] The method according to [1], in which the test target used to treat each cell is associated with a phenotype of each cell.

[3] The method according to [1] or [2], in which the identifying step further includes a step of identifying a target site at which a desired phenotypic change of the cells is produced by the test target.

[4] The method according to any one of [1] to [3], further including a step of analyzing genome-related information of each cell.

[5] The method according to any one of [1] to [4], in which the step of preparing cells includes a step of associating the first barcode nucleic acid with cells by mixing a liquid medium including the test target and the first barcode nucleic acid with the cell.

[6] The method according to any one of [1] to [5], in which the step of preparing cells includes a step of associating the first barcode nucleic acid with the test target by adding hydrogel beads to a liquid medium including the test target and the first barcode nucleic acid to generate a first sub-compartment including the test target and the first barcode nucleic acid.

[7] The method according to any one of [1] to [6], in which the step of preparing cells includes fusing a first sub-compartment including the test target and the first barcode nucleic acid and a second sub-compartment including the cell to generate a compartment including the test target, the first barcode nucleic acid, and the cell.

[8] The method according to [7], in which the step of preparing cells includes treating the cells with the test target in the compartment.

[9] The method according to any one of [6] to [8], in which the compartment or sub-compartment is a droplet.

[10] The method according to any one of [7] to [9], in which the step of preparing cells includes a step of recovering the cells from the compartment.

[11] The method according to any one of [1] to [10], in which the sorting step includes a step of sorting cells in which a predetermined reaction occurs due to the test target, based on cellular phenotype.

[12] The method according to any one of [4] to [11], in which the step of analyzing genome-related information includes
a step of preparing a plurality of compartments including a genome-related nucleic acid corresponding to a cell genome or a derivative thereof, the first barcode nucleic acid, and a second barcode nucleic acid linking bead, in which the second barcode nucleic acid linking bead includes a plurality of second barcode nucleic acids hybridizable with the cell genome or the genome-related nucleic acid corresponding to a derivative thereof or the first barcode nucleic acid,
a step of obtaining a hybridized complex by hybridizing each of the genome-related nucleic acid and the first barcode nucleic acid, with the second barcode nucleic acid,
a step of producing an amplified product derived from the hybridized complex, and
a step of detecting genome-related information of the cell after its coexistence with the test target using an expression pattern of the amplified product as an indicator.

[13] The method according to [12], in which the genome-related nucleic acid is cell genome DNA, or RNA derived from the cell genome or cDNA thereof.

[14] The method according to any one of [12] or [13], in which each first barcode nucleic acid includes a first common barcode region which is common to the same test target and a first hybridization region hybridizable with the second barcode nucleic acid.

[15] The method according to any one of [12] to [14], in which sequence information of the first common barcode region is an indicator for specifying the test target.

[16] The method according to any one of [12] to [15], in which each of the plurality of second barcode nucleic acids linked to the second barcode nucleic acid linking bead includes a second common barcode region which is common to each other, a second unique barcode region able to be distinguished from each other, and a second hybridization region hybridizable with the genome-related nucleic acid or the first barcode nucleic acid.

[17] The method according to any one of [12] to [16], in which sequence information of the second unique barcode region is an indicator for specifying the genome-related nucleic acid.

[18] The method according to any one of [11] to [16], in which the second barcode nucleic acid further includes a PCR primer region.

[19] The method according to any one of [12] to [17], in which the second hybridization region includes a nucleic acids complementary to the first hybridization region or the genome-related nucleic acid.

[20] The method according to any one of [1] to [19], in which the imaging cell sorter is an analysis apparatus provided with an analysis unit in which scattered light, transmitted light, fluorescent light, or electromagnetic waves from an observation object present in a light-irradiated region irradiated with light from a light source are received and converted to electrical signals by a light receiving unit and the observation object is analyzed based on signals extracted in time sequence from the electrical signals which are output from the light receiving unit.

[21] The method according to [20], in which an optical modulation unit having a plurality of regions with different optical characteristics from each other is arranged on an optical path between the light source and the light-irradiated region.

[22] The method according to [20] or [21], further including an optical system control unit which controls the light source based on analysis results of analysis carried out by the analysis unit.

[23] The method according to [22], in which the light from the light source has a plurality of optical regions, and the optical system control unit controls an optical structure of the optical regions.

[24] The method according to any one of [20] to [23], in which the analysis unit updates a classification algorithm based on analysis results.

[25] The method according to any one of [20] to [24], in which the light and the light-irradiated region are controlled based on results of analysis carried out by the analysis unit.

[26] The method according to any one of [20] to [25], in which the imaging cell sorter includes a flow cell including the light-irradiated region.

[27] The method according to any one of [20] to [26], in which the imaging cell sorter has a sorting unit which classifies the observation object and sorts the observation object, based on analysis results of the analysis unit.

[28] The method according to any one of [20] to [27], in which the imaging cell sorter is further provided with a flow line width control unit by which a flow line width of the observation object moving in a flow path is variably controlled, and a teacher information generating unit which generates teacher information indicating criteria for classifying a state of the observation object by machine learning based on a signal extracted in time sequence and a flow line width when the signal is acquired, the analysis unit estimates a state of the observation object moving in the flow line based on the signal and the teacher information generated by the teacher information generating unit.

[29] The method according to [28], in which the flow line width control unit controls the flow line width to a first flow line width which is a width corresponding to a diameter of the observation object, the teacher information generating unit generates, as the teacher information, first teacher information based on a first observation result signal detected by the light receiving unit at the first flow line width controlled by the flow line width control unit, and the analysis unit estimates a state of the observation object moving in the flow line based on the first teacher information generated by the teacher information generating unit and the signal.

[30] The method according to [28] or [29], in which the flow line width control unit controls the flow line width to a second flow line width which is a width based on a diameter of the observation object and which is wider than the first flow line width, the teacher information generating unit further generates, as the teacher information, second teacher information based on a second observation result signal detected by the light receiving unit at the second flow line width controlled by the flow line width control unit, and the analysis unit estimates a state of the observation object moving in the flow line based on the first teacher information generated by the teacher information generating unit, the second teacher information generated by the teacher information generating unit, and the signal.

[31] The method according to any one of [1] to [30], in which the imaging cell sorter is provided with at least one flow path through which the observation object flows, a light source for irradiating the flow path with cingulate excitation light, an imaging unit which obtains photographic images of a certain cross-section of the observation object by obtaining fluorescence from the observation object which passes through a position irradiated with the excitation light, and a three-dimensional image generating unit which generates a three-dimensional photographic image of the observation object based on a plurality of photographic images of cross-sections obtained by the imaging unit.

[32] The method according to [31], in which the imaging cell sorter sorts the observation objects based on information indicating a morphology of the observation object shown in the cross-sectional photographic images obtained by the imaging unit.

[33] The method according to [31] or [32], in which the flow path is a plurality of flow paths lined up in parallel, the plurality of flow paths are irradiated with the excitation light, and the imaging unit obtains cross-sectional photographic images of the observation object flowing through each of the plurality of flow paths.

[34] The method according to any one of [1] to [33], in which an optical modulation unit having a plurality of regions with different optical characteristics from each other is arranged on an optical path between the light source and an image sensor which detects an intensity of the fluorescence, and the imaging unit reconstructs an image of the cross-section of the observation object as a captured photographic image based on the intensity of the fluorescence detected by the image sensor and the optical characteristics of the optical modulation unit.

[35] The method according to any one of [1] to [34], in which the test target includes a test substance.

[36] The method according to any one of [1] to [35], in which the test target is a test substance.

[37] The method according to any one of [1] to [36], in which the step of analyzing genome-related information includes a step of preparing a plurality of compartments including a cell exhibiting a desired phenotypic change which was sorted using an imaging cell sorter, the first barcode nucleic acid, and second barcode nucleic acid linking beads, in which the second barcode nucleic acid linking beads include a plurality of second barcode nucleic acids hybridizable with the genome-related nucleic acid corresponding to the cell genome or derivatives thereof or the first barcode nucleic acid, a step of obtaining a hybridized complex by hybridizing each of the genome-related nucleic acid and the first barcode nucleic acid with the second barcode nucleic acid, a step of generating amplified products derived from the hybridized complex described above, and a step of detecting genome-related information after the coexistence of the first barcode nucleic acid and the test target with the cell, using the expression pattern of the amplified products described above as indicators.

EXAMPLES

A specific description will be given below of the present disclosure based on Examples, but the present disclosure is not limited to such Examples. In addition, unless particularly noted, the measurement methods and units of the present disclosure conform to the provisions of the Japanese Industrial Standards (JIS).

Reference Example 1: Preliminary Test for Linking First Barcode Nucleic Acid to Cells In accordance with the Multi-seq method (described in Nature Methods, volume 16, pages 619-626 (2019)), the following preliminary experiments were performed using the same cells, anchor CMOs, co-anchor CMOs, and oligonucleotides as in Example 1 described below. That is, cells and an anchor CMO were incubated in a Phosphate Buffered Saline (PBS) solution at 4 degrees for 5 minutes, then a co-anchor CMO was added thereto and incubation was further performed at 4 degrees for 5 minutes, and, finally, a red fluorescent dye (Cy5) conjugated oligonucleotide (having sequences corresponding to partial sequences of the first barcode nucleic acid) was mixed therein and incubation was performed at 4 degrees for 5 minutes.

As a result, as shown in FIGS. 4A and B, in the PBS solution, the red fluorescent dye (Cy5) conjugated oligonucleotide (having a sequence corresponding to a partial sequence of the first barcode nucleic acid) was retained in the cells after a short time of incubation (30 minutes after incubation). However, it was confirmed that when a longer time (3 hours or longer after incubation) passed, there were cases where almost all of the cells were dead or the added barcode nucleic acid fell off the cells (not shown).

Reference Example 2: Preliminary Test for Linking First Barcode Nucleic Acid to Cells In addition, a preliminary experiment was performed using the same method as in Reference Example 1, except that the incubation was carried out using a cell medium containing serum or Bovine Serum Albumin (BSA) as a solvent. As a result, it was confirmed that the attachment rate of the red fluorescent dye (Cy5) conjugated oligonucleotide (having a sequence corresponding to a partial sequence of the first barcode nucleic acid) to the cells was reduced, as shown in the photographs in C and D of FIG. 4.

Reference Example 3: Preliminary Test to Associate First Barcode Nucleic Acid with Cells In addition, a preliminary experiment was performed using the same method as in Reference Example 1, except that, when adding anchor CMOs and co-anchor CMOs, the solution was changed to a serum-free Opti-MEM medium (manufactured by Thermo Fisher) and the incubation was carried out at room temperature. As a result, it was confirmed that an fluorescent dye conjugated oligonucleotide (having a sequence corresponding to a partial sequence of the first barcode nucleic acid) can be attached sufficiently to the cells, as shown in the photographs in E and F of FIG. 4. The results demonstrated that it is possible to perform a reaction suitable for a droplet screening in conditions of keeping high efficiency for attaching the fluorescent dye conjugated oligonucleotide to cells (100%). Then, the experiment of Example 1 below was performed.

Example 1: Association of First Barcode Nucleic Acid with Cells in a Compartment (Tube)

In this experiment, first, in a tube 1, two types of cholesterol-modified oligonucleotide linkers, that is, anchor CMO (5'-Cholesterol-TEG-GTAACGATGGAGCTGTCACTTG-GAATTCTCGGGTGCCAAGG-3' (sequence number 1)) and a co-anchor CMO (5'-AGTGACAGCTGGATCGT-TAC-TEG Cholesterol-3' (sequence number 2)) were mixed. Here, as the "Cholesterol-TEG" in the oligonucleotide linker, a commercial product listed at https://sg.idtdna.com/site/Catalog/Modifications/Product/2555 was used. In the mixing process described above, as the solvent, a serum-free Opti-MEM medium was used and the final concentrations of both the anchor CMO and the co-anchor CMO were set to 250 nM. The tube 1 was incubated for 5 minutes at room temperature.

Next, first barcode nucleic acid A was added to the tube 1, mixed, and incubated. The oligonucleotide including the first barcode nucleic acid A sequence (8 bases) was 5'-CCTTGGCACCCGAGAATTCCACCACAATGA30-3 (sequence number 3). Here, A30 added to the end of the first barcode nucleic acid A is polyadenine formed of 30 residues (poly($A_{30}$)). The final concentration of the first barcode nucleic acid A was set to 250 nM and the incubation was carried out for 5 minutes at room temperature.

Next, cells collected by centrifugation in advance were added to the tube 1 and incubated. The cells used at this time were THP1 cells and the cell concentration was set to $1\times10^7$ cells/mL. The incubation was carried out for 5 minutes at room temperature.

On the other hand, in a tube 2, cells were tagged with the first barcode nucleic acid B according to the same method and conditions as in the tube 1, except that oligonucleotide including first barcode nucleic acid B (8 bases) was used instead of the oligonucleotide including first barcode nucleic acid A (8 bases). The oligonucleotide including the first barcode nucleic acid B (8 bases) was 5'-CCTTGGCACCCGAGAATTCCATGAGACCTA30-3' (sequence number 4).

Example 2: Association of Test Substance, First Barcode Nucleic Acid and Cells in a Compartment (Tube)

Cells were resuspended in RPM1-1640 medium with 10% FBS and 50 μM 2-mercaptoethanol in the tube 1 and the tube 2, respectively. Next, as a drug, lipopolysaccharide (LPS) suspended in dimethyl sulfoxide (DMSO) was added to tube 1 only, at a final concentration of 2 μg/mL. In the tube 2, only DMSO, the solvent for the drug, was added. Next, the tube 1 and the tube 2 were incubated for 2 hours at 37 degrees in $CO_2$, respectively. Through the experiment up to here, the drug condition whether the drug LPS is present or not, was respectively associated to each of the cells by corresponding each cell to the first barcode nucleic acid type A or the second barcode nucleic acid type B.

In the method of Example 2, it was also confirmed that the problem that the barcode nucleic acids attached to the cells were falling off the cells during incubation for a long time is avoidable by resuspending and culturing the cells in RPM1-1640 medium with 10% FBS and 50 μM 2-mercaptoethanol.

Specifically, cells tagged with a green fluorescent dye FAM conjugated oligonucleotide (having a sequence corresponding to a partial sequence of the first barcode nucleic acid) and cells tagged with a red fluorescent dye (Cy5) conjugated oligonucleotide (having a sequence corresponding to a partial sequence of the first barcode nucleic acid) were prepared separately, mixed in PBS solution, and incubated for one hour. When the mixed cell samples after this incubation were observed through respective channels of green fluorescence (A in FIG. 5) and red fluorescence (B in FIG. 5) using a fluorescent light microscope, many of the cells glowed in both green and red. That is, when culturing cells in the PBS solution for a long time, which was the previous method, the barcode nucleic acid fell off the cells and the two types of barcode nucleic acids were mixed together.

Next, in the same manner, cells tagged with a green fluorescent dye FAM conjugated oligonucleotide (having a sequence corresponding to a partial sequence of the first barcode nucleic acid) and cells tagged with a red fluorescent dye (Cy5) conjugated oligonucleotide (having a sequence corresponding to a partial sequence of the first barcode nucleic acid) were prepared separately, mixed in a RPMI-1640 medium with 10% FPS and 50 μM 2-mercaptoethanol and incubated for one hour. When the mixed cell samples after this incubation were observed through respective channels of green fluorescence (C in FIG. 5) and red fluorescence (D in FIG. 2) using a fluorescent light microscope, it was confirmed that the barcodes did not fall off the cells, and the problem of the two types of barcode nucleic acids mixing together was solved.

In addition, the barcode nucleic acid added to the cells described above remained attached to the surface of the cell membrane for approximately an hour after the addition and then the cells to which the barcode nucleic acid was added were observed over time (after 1 hour, 2 hours, 3 hours, and 6 hours). As a result, as shown in FIG. 6, a part thereof was taken up into the cells and the cells held the barcode nucleic acid as it was. In addition, it was confirmed that culturing the cells in RPM1-1640 medium with 10% FBS and 50 μM 2-mercaptoethanol makes it possible to prevent the death of the cells to which the barcode nucleic acid was added.

Example 3: Experiments of Fixation, Protein Labeling, and Staining of the Cells Responding to a Test Substance Next, some cells were collected from the tube 1 and the tube 2, respectively. The obtained cells were fixed by incubating them in 4% formalin solution suspended in PBS for 15 minutes at room temperature or with 1 mg/mL DTSSP solution (Dithiobis sulfosuccinimidyl propionate disodium salt, (DTSSP) (manufactured by DOJINDO) for 30 minutes at room temperature, and then treated with ice-cold methanol for 5 minutes. The immobilized cells were replaced in the PBS solution. Thereafter, immunostaining was performed using a primary antibody with respect to NFκB protein (NFκB p65 (D14E12), manufactured by CST). The primary antibody was used after 100-fold dilution and the reaction solution was treated with PBS including 1% BSA at 4 degrees for 16 hours to 20 hours. Next, a reaction was carried out with a secondary antibody conjugated to a fluorescent dye (Alexa Fluor 488). The secondary antibody was used after 200-fold dilution and the reaction solution was treated with PBS including 1% BSA at room temperature for one hour.

Figure 7:
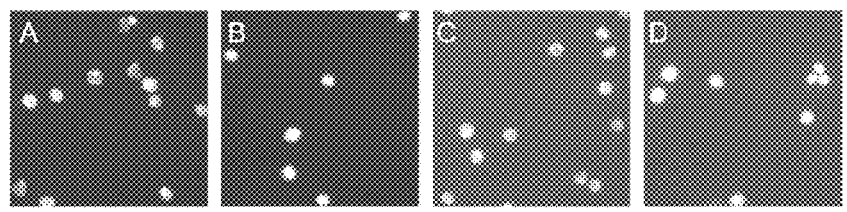
FIG. 7 is photographs when the degree of dyeing and distribution changes of NFκB protein were observed in the cells in which immuno-antibody staining was performed with primary antibodies against the NFκB protein and secondary antibodies conjugated to a fluorescent dye (Alexa Fluor 488) after formalin fixation or DTSSP fixation.

When confirmation was carried out using a fluorescent light microscope, as shown in FIG. 7, in the cells of tube 2, to which only DMSO, the solvent of the drug, was added, almost all of the NFκB protein was localized in the cytoplasm, while in the cells of the tube 1, to which the LPS drug was added, almost all of the NFκB protein was localized in the nucleus.

Next, some cells collected from the tube 1 were stained with Fixable Far Red. Then, these stained cells were mixed with some cells collected from the tube 2, which were not stained with Fixable Far Red, to obtain a mixed cell solution A, so that both two type of cells were contained at a concentration of 1:1.in the mixed cell solution.

In addition, as a negative control, some cells were collected from the tube 2 to which only DMSO was added, which was the solvent of the drug, to obtain a cell solution B.

In addition, a part of the mixed cell solution A was also prepared to obtain training data of the imaging cell sorter.

Example 4: An Experiment in which Cells Responding to a Test Substance were Sorted Based on Cellular Image Phenotype by an Imaging Cell Sorter Using an imaging cell sorter, cells were sorted and recovered from a mixed cell solution based on the nuclear localization of the NFκB protein, which is a cellular image phenotype observed in response to the addition of LPS drug. The imaging cell sorter used in this experiment was the sorter described in Science, 15 Jun. 2018: Vol. 360, Issue 6394, pp. 1246-1251.

First, a machine learned model was developed to classify cells where nuclear localization of the NFκB protein occurred, which was the cellular image phenotype to be sorted and recovered. Specifically, a supervised machine learned model (SVM: Support Vector Machine) was generated using a part of the mixed cell solution A for training, in which cells from the tube 1 and cells from the tube 2 (only the cells from the tube 1 were stained with Fixable Far Red) were mixed in a known ratio. The part of the mixed cell solution A was introduced into the imaging cell sorter to obtain image signals derived from Alexa Fluor 488 which is used for the labeling of the NFκB protein. A classification model to predict the nuclear localization of NFκB protein was generated using the image signals and the correct answer data based on the label of Fixable Far Red as training data.

Next, sorting of cells from cell solution A, in which cells to which the LPS drug was added and cells to which the drug was not added were mixed at the cell concentration of 1:1, was carried out using an imaging cell sorter based on the nuclear localization of the NFκB protein, which was the cellular image phenotype of the cells to which the LPS drug was added, and the cells where nuclear localization of the NFκB protein occurred were recovered. The recovery ratio was 90% or more of the total cells.

Figure 8:
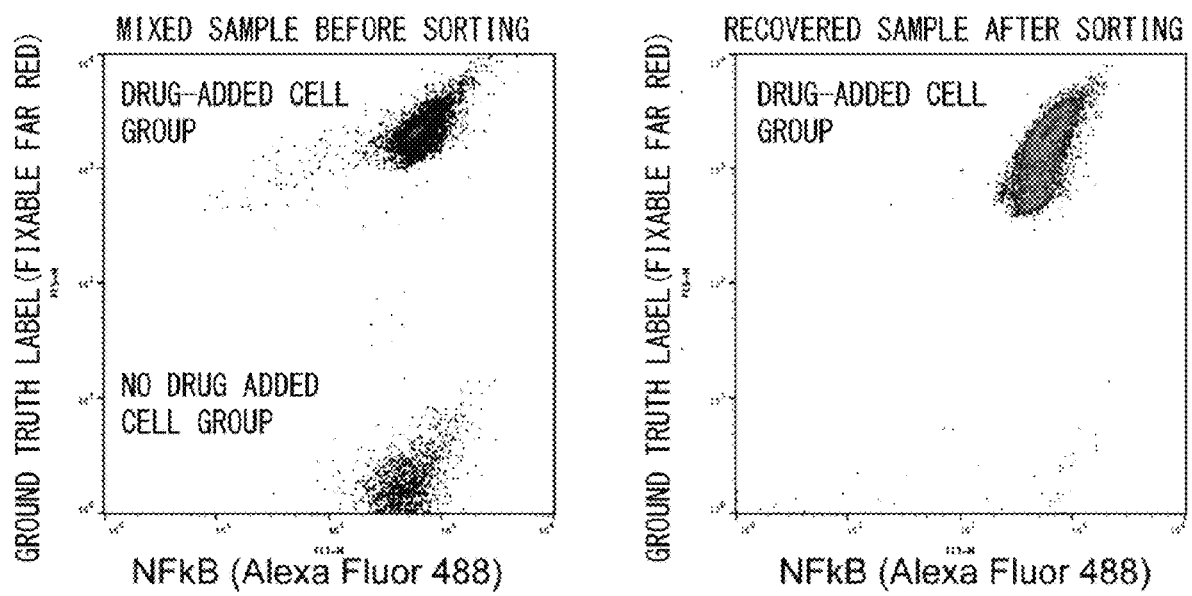
FIG. 8 is graphs showing the results of measuring and quantifying the purity of a group of cells based on a ground truth label signal derived from Fixable Far Red by flow cytometry. The horizontal axis is the fluorescent intensity derived from the immunostaining of NFκB protein and the vertical axis is the fluorescent intensity derived from the Fixable Far Red, which is used to label correct answer.

For samples for which protein labeling was performed after 4% formalin fixation, nuclear localization of the NFκB protein was predicted from the image signal data and the prediction was correlated with the correct answer based on the label signal derived from Fixable Far Red. Consequently, the classification accuracy of 0.95 for acc (Accuracy) and 0.997 for roc-auc (Area under the Receiver Operating Characteristic Curve) was obtained. Furthermore, after sorting based on image signal data, the purity of the recovered sample after sorting was measured and quantified based on the label signal derived from Fixable Far Red by flow cytometry. The results were as shown in FIG. 8, and the rate of the cells receiving drug addition in the recovered sample after sorting, (positive purity) was obtained to be 0.995.

Figure 9:
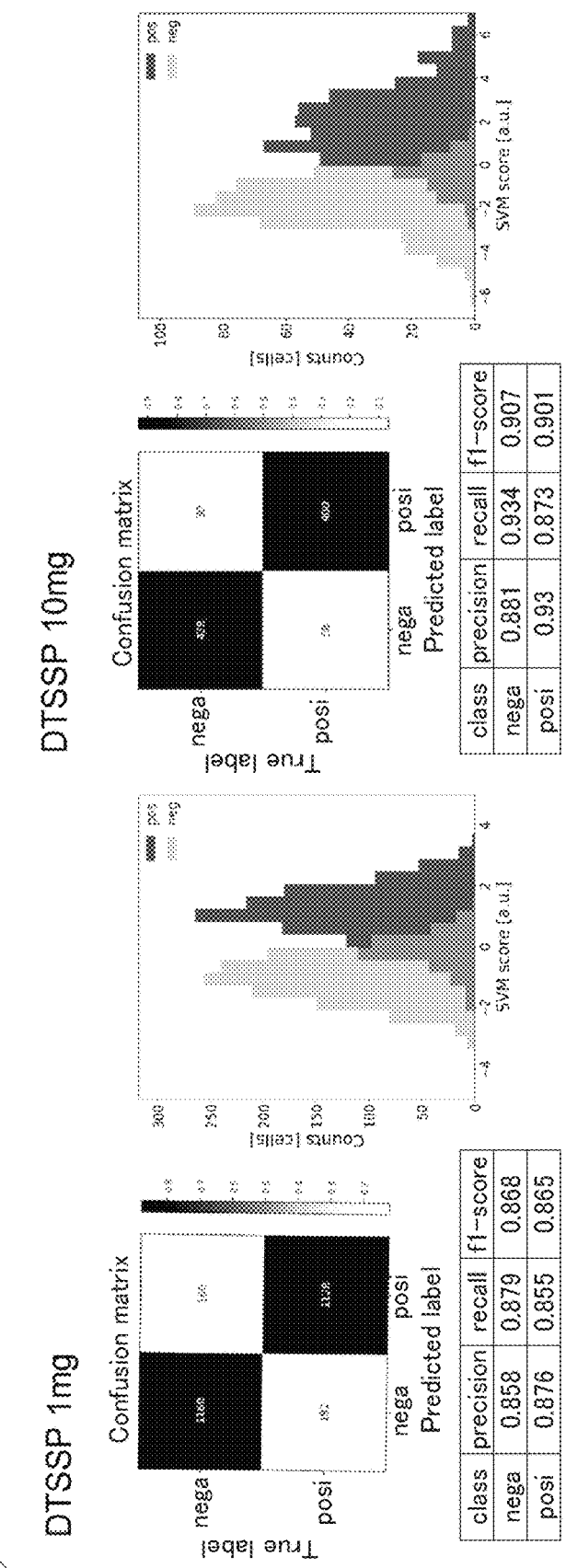
FIG. 9 shows matrixes and tables, showing SVM (Support Vector Machine) scores (histograms) and the results comparing the prediction results with true data labeled by Fixable Far Red labeling for each of the cell group under the fixation condition of 1 mg or 10 mg DTSSP. SVM is a kind of machine learning model. The machine learning was performed regarding the presence or absence of nuclear localization of NFκB protein (nuclear localization was positive and no nuclear localization was negative) obtained from image signal data.

For samples for which protein labeling was performed after DTSSP fixation, prediction of nuclear localization of the NFκB protein was made from the image signal data and the prediction was correlated with the correct answer based on the label signal derived from the Fixable Far Red. The results were as shown in FIG. 9. Under a fixation condition of 1 mg DTSSP, a classification accuracy of 0.87 for acc (Accuracy) and 0.91 for roc-auc was obtained. Under a fixation condition of 10 mg DTSSP, a classification accuracy of 0.90 for acc (Accuracy) and 0.96 for roc-auc was obtained.

From the above results, it can be seen that, it is possible in the present method to sort cells rapidly based on the image phenotype using imaging cell sorters, while cell sorting based on the image phenotype is time-consuming and costly in the method of the related art.

Example 5: An Experiment to Confirm Information Connectedness Between Test Substance and Cellular Phenotype of the Cells Sorted and Recovered by Imaging Cell Sorter From cells (positive purity: 0.995) sorted and recovered by the imaging cell sorter and control mixture cells (the ratio of LPS drug present to drug absent was 1:1), solutions including approximately 4,800 cells were dispensed and single cell analysis was performed for each cell. To read out the DNA barcodes modified for each cell, a single cell analysis technology using a droplet technique, in particular the Chromium Controller apparatus and the Single Cell 3' Reagent Kit v3 manufactured by 10× Genomics, was used.

Figure 10:
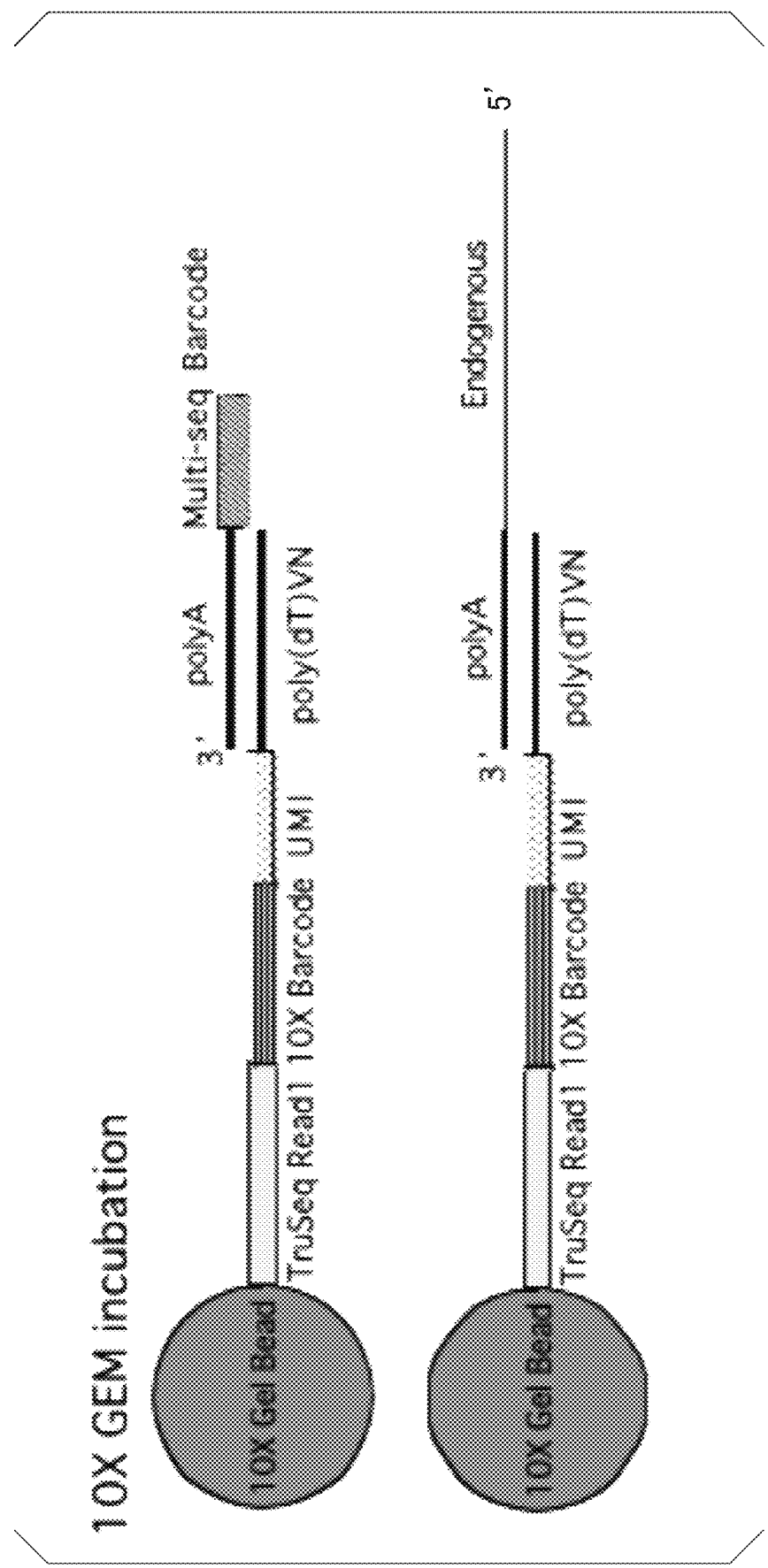
FIG. 10 is a schematic diagram showing a part of the reagents used for the genetic analysis technique in Examples 5 and 6. In the diagram, Multi-seq Barcode, 10× Barcode, and UMI correspond to the first barcode sequence, the second common barcode region, and the second unique barcode region sequence, respectively. The second barcode nucleic acid is hybridized with the first barcode nucleic acid, or the second barcode nucleic acid is hybridized with the cell genome or the genome-related nucleic acid corresponding to derivatives thereof.

FIG. 10 shows a schematic diagram of a reagent included in the reagent kit. In the technique a large number of droplets are generated in a micro flow path and one second barcode nucleic acid linking bead which is different for each droplet and one cell are stochastically contained at a ratio of 1:1 in each of the droplets. A plurality of second barcode nucleic acids are linked to the second beads via a linker. Furthermore, each of the plurality of second barcode nucleic acids linked to a second bead includes a second common barcode region (16 bases), which are common to each other as long as the cells included in the droplet are the same, a second unique barcode region (12 bases) able to be distinguished from each other for each individual droplet, and a second hybridization region hybridizable with the genome-derived nucleic acid of the cell or the first barcode nucleic acid.

Specifically, first, in each droplet, a second hybridized poly(dT) sequence added to the end of the second unique barcode region was bound to a poly(A) end of the first barcode nucleic acid attached to the surface of the cell. Furthermore, a reverse transcription reaction using reverse transcriptase or the like was performed, and the complementary strand DNA of the first barcode nucleic acid which are bound to the second barcode nucleic acid sequence was generated using the first barcode primer 5'-CTTGGCACCCGAGAATTCC-3' (sequence number 5) and a complementary strand DNA primer included in the Single Cell 3' Reagent Kit v3 manufactured by 10× Genomics.

Thereafter, each of the generated droplets was disrupted in a mixed state, and a group of complementary strand DNAs to the second unique barcodes which were extracted from each droplet was amplified by a PCR reaction, and the DNA concentration was measured with a Qubit Fluorometer manufactured by Invitrogen. The results were 23.4 ng/μl for the image-sorted and recovered cell solution and 30.4 ng/μl for control cell solution.

Figure 11:
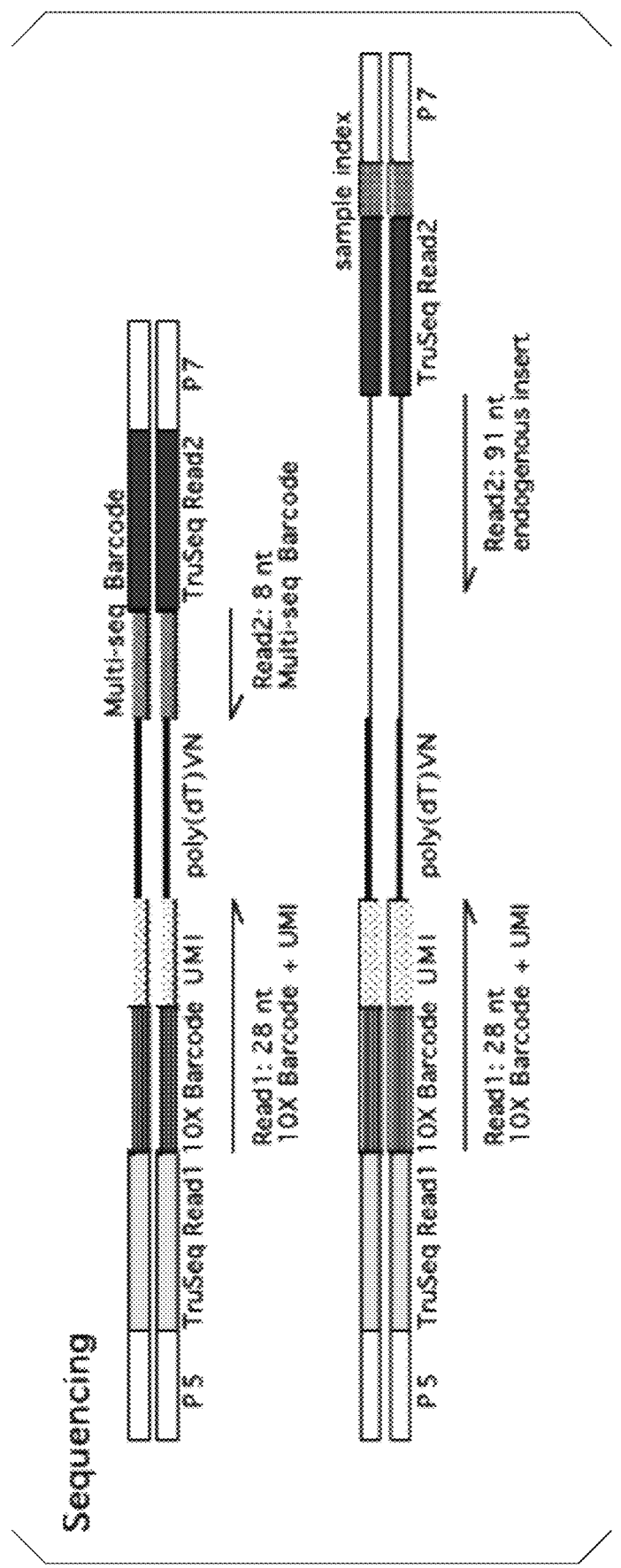
FIG. 11 is a schematic diagram of a sequence library after a PCR reaction applied in Examples 5 and 6.

Next, as shown in FIG. 11, a next-generation sequence library of the first barcode nucleic acid, to which a second barcode nucleic acid sequence which was different for each cell was bound, was generated by a PCR reaction. The used primers were as follows:
Read1 side (Universal 15 primer) 5'-AATGA-TACGGCGACCACCGAGATCTACACTCTTTCCCTA-CACGACGCTCTTCC GATCT-3' (sequence number 6),
Read2 side (TruSeq RPI primer)
in the image-sorted and recovered cell solution, 5'-CAAGCAGAAGACGGCATACGAGATAT-TGGCGTGACTGGAGTTCCTTGGCACC CGAGAAT-TCCA-3' (sequence number 7), and,
in the control cell solution, 5'-CAAGCAGAAGACGGCAT-ACGAGATTACAAGGTGACTGGAGTTCCTTGGCACC CGAGAATTCCA-3' (sequence number 8).

For the obtained next-generation sequence library, the DNA size and concentration were measured using D5000 screen tape manufactured by Agilent to confirm the quality of the library.

P5 and P7 sequence libraries were generated using a MiSeq Reagent Kit v3 manufactured by Illumina and a MiSeq next-generation sequencer manufactured by Illumina was used for next-generation sequencing. The obtained sequence data were read out as text-based FASTQ files on each of the Read1 side and Read2 side and analyzed using Python3, DropseqTools, and UMITools.

As a result, for the image-sorted and recovered cells, the total number of reads of the second common barcode region sequence (16 bases) and the second unique barcode region (12 bases) was 19,912,682. Furthermore, the number of first barcode nucleic acid sequences which can be associated with the second common barcode region sequence (16 bases) and the second unique barcode region (12 bases) was 16,354,670. Among the above, the number of reads of the first barcode nucleic acid A which was associated with the presence of the drug LPS was 85.1% of the total number of first barcode nucleic acid reads, and the number of reads of the first barcode nucleic acid B which was associated with the absence of the drug was 0.8% of the total number of first barcode nucleic acid reads.

For the control mixture cells (the ratio of the cells LPS drug present to drug absent was 1:1), the total number of reads of the second common barcode region (16 bases) and the second unique barcode region (12 bases) was 10,795,154, and the number of first barcode nucleic acid sequences which can be associated with the second common barcode region (16 bases) and the second unique barcode (12 bases) was 7,587,061. Among the above, the number of reads of the first barcode nucleic acid A which was associated with the presence of the drug LPS was 51.3% of the total number of first barcode nucleic acid reads, and the number of reads of the first barcode nucleic acid B which was associated with the absence of the drug was 35.6% of the total number of first barcode nucleic acid reads.

By this series of experiments, it was confirmed that, using the imaging cell sorter, it is possible to perform a cellular phenotypic screening of the test substances by sorting cells to which nucleic acid barcodes associated with the test substances were attached based on the cellular image phenotype observed in response to the test substance and reading the nucleic acid barcode sequence attached to the sorted cells.

Example 6: An Experiment to Confirm Connecting Information of Test Substance and Cellular Phenotype with Gene Expression Information in Mixed Cells A sample which mimics the cell mixture sample sorted and recovered by the imaging cell sorter (a ratio of cells where the LPS drug was present to where the drug was absent was 9:1) (positive purity: 0.9) was prepared by the above fixation, labeling, and staining fixation conditions. A solution including approximately 4,800 cells was dispensed from the sample and single cell analysis was performed thereon. To read out the DNA barcodes which modify each cell and cell-derived genetic information, a single cell analysis technology using a droplet technique, in particular the Chromium Controller apparatus and the Single Cell 3' Reagent Kit v3 manufactured by 10× Genomics, was used as described in Example 5.

First, in each droplet, the second hybridization region of poly(dT) sequence added to the end of the second unique barcode region was bound to the poly(A) end of the first barcode nucleic acid attached to surface of the cell. Furthermore, a reverse transcription reaction using reverse transcriptase or the like was performed, and the complementary strand DNA of the first barcode nucleic acid which are bound to the second barcode nucleic acid sequence was generated using a primer 5'CTTGGCACCCGAGAATTCC-3' (sequence number 5) for the first barcode nucleic acid and the complementary strand DNA primer included in the Single Cell 3' Reagent Kit v3 manufactured by 10× Genomics.

In addition, at the same time as generating the complementary strand DNA of the second unique barcode, for the endogenous cDNAs of each cell, the second hybridized poly(dT) sequences added to the end of the second unique barcode regions were bound to the poly(A) end of the cell-derived mRNAs. Furthermore, a reverse transcription reaction using reverse transcriptase or the like was performed and cell-derived complementary strand DNA was generated using complementary strand DNA primers included in the Single Cell 3' Reagent Kit v3 manufactured by 10× Genomics.

Thereafter, each of the generated droplets was disrupted in a mixed state, and the complementary strand DNA of the first barcode nucleic acid to which the second barcode nucleic acid sequence and the group of cell-derived complementary strand DNAs were extracted from each of the droplets. Thereafter, the each of the complementary strand DNAs were amplified by a PCR reaction, and their DNA concentration was measured by a Qubit Fluorometer manufactured by Invitrogen. As a result of the measurement, the concentration of barcode complementary strand DNA of the cells recovered after image sorting was 57.8 ng/μl, and the concentration of cell-derived complementary strand DNA was 0.676 ng/μl.

Using the same method, the barcode complementary strand DNA and the cell-derived complementary strand DNA were also recovered, respectively, from the negative control cells to which no LPS drug stimulation was given, and the DNA concentrations were similarly measured with the Qubit Fluorometer manufactured by Invitrogen. As a result of the measurement, the concentration of barcode complementary strand DNA was 45.6 ng/μl and the concentration of cell-derived complementary strand DNA was 0.658 ng/μl.

Next, a next-generation sequence library of first barcode nucleic acid and cell-derived complementary strand DNAs to which second barcode nucleic acid sequences different for each cell were bound was generated by a PCR reaction. The primers used were as follow:

Read1 side (Universal 15 primer) 5'-AATGA-TACGGCGACCACCGAGATCTACACTCTTTCCCTA-CACGACGCTCTTCC GATCT-3' (sequence number 6), and, Read2 side (TruSeq RPI primer) for the negative control cells, 5'-CAAGCAGAAGACGGCATACGAGATAT-TGGCGTGACTGGAGTTCCTTGGCACC CGAGAAT-TCCA-3' (sequence number 7), and, Read2 side for image sorted recovered cells, 5'-CAAGCAGAAGACGGCATACGAGATTA-CAAGGTGACTGGAGTTCCTTGGCACC CGAGAAT-TCCA-3' (sequence number 8).

For the obtained next-generation sequence library, the DNA size and DNA concentration were measured using D5000 screen tape manufactured by Agilent and qPCR reactions, and the quality of the library was confirmed.

P5 and P7 sequence libraries were generated using the MiSeq Reagent Kit v3 manufactured by Illumina, and the MiSeq next-generation sequencer manufactured by Illumina was used for next-generation sequencing. The obtained sequence data were read out as each text-based FASTQ files of the Read1 side and Read2 side and analyzed using Python3, DropseqTools, and UMITools.

Figure 13:
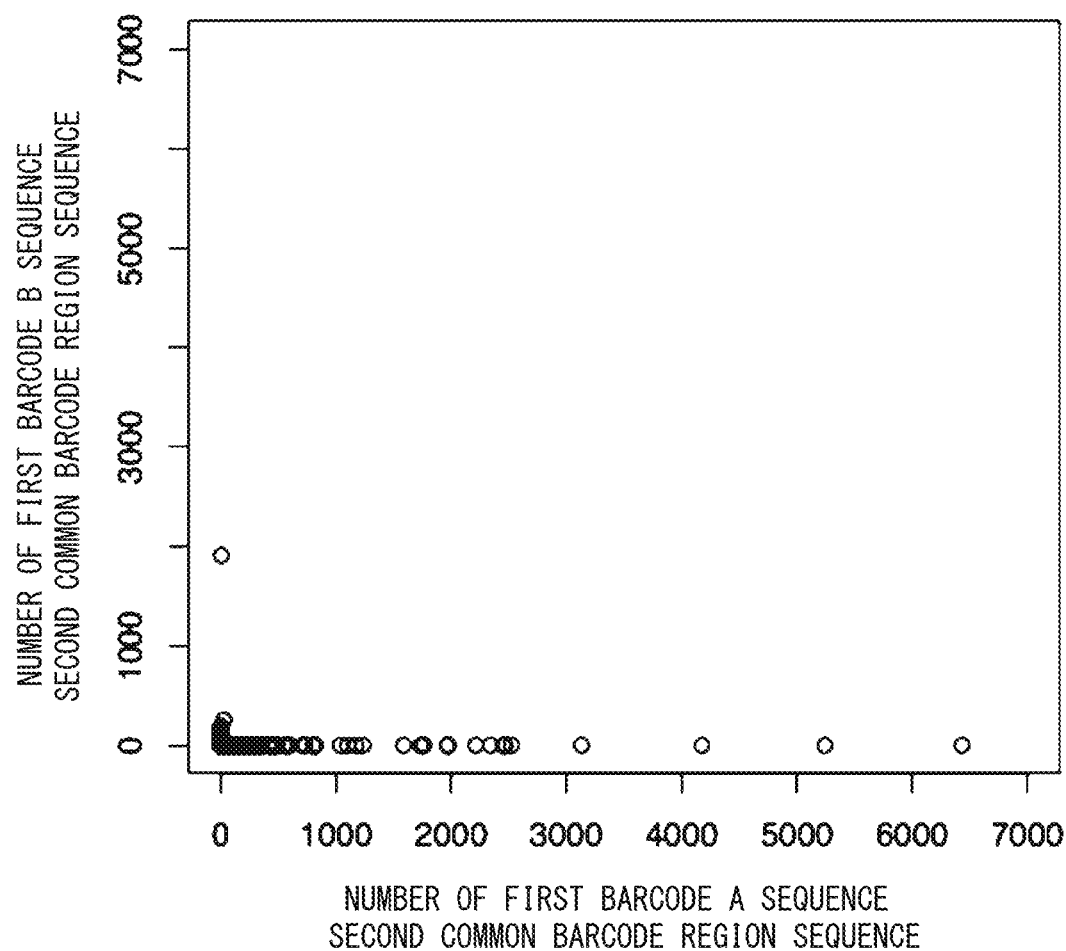
FIG. 13 is a graph (Graph 1) which, for each second unique barcode region sequence of the first barcode sequence side data where the second unique barcode region sequence matched the complementary strand DNA side data, represents the distribution of the number of reads of the first barcode nucleic acid sequence (two types) detected from the unique reads having the above (mixed sample (the ratio of cells where the LPS drug was present to where the drug was absent was 9:1)) (first barcode nucleic acid sequence A: LPS drug absent, first barcode nucleic acid sequence B: LPS drug present).

As a result, the total number of reads of the second common barcode region sequence (16 bases) and the second unique barcode region (12 bases) from the mixed sample cells (the ratio of cells where the LPS drug was present to where the drug was absent was 9:1) was 251,958. Furthermore, the number of first barcode nucleic acid sequences associated with the second common barcode region sequence (16 bases) and the second unique barcode region (12 bases) by reading concurrently was 249,793. Among the above, the number of reads of the first barcode nucleic acid A corresponding to the presence of the drug LPS was 86.8% of the total number of first barcode nucleic acid reads and the number of reads of the first barcode nucleic acid B corresponding to the absence of the drug was 3.1%. Furthermore, after read error correction was carried out, among the number of reads of the second common barcode region sequences read out corresponding to the first barcode nucleic acid sequence A or the first barcode nucleic acid sequence B, the upper list where the second common barcode region sequences having a large number of reads are arranged in order is shown together with the number of reads of the first barcode nucleic acid sequence A or the first barcode nucleic acid sequence B which are read out concurrently (Table 1-1 in FIG. 12A and Table 1-2 in FIG. 12A). In addition, among the 594 second unique barcode region sequences of the complementary strand DNAs, 550 identical sequences to the second unique barcode region sequences were found in the first barcode sequence library, and almost all (92.6%) of the first nucleic acid barcode sequence library in which the second unique barcode region sequence was found were attributed to the first barcode nucleic acid A (FIG. 13, Graph 1).

Figure 15:
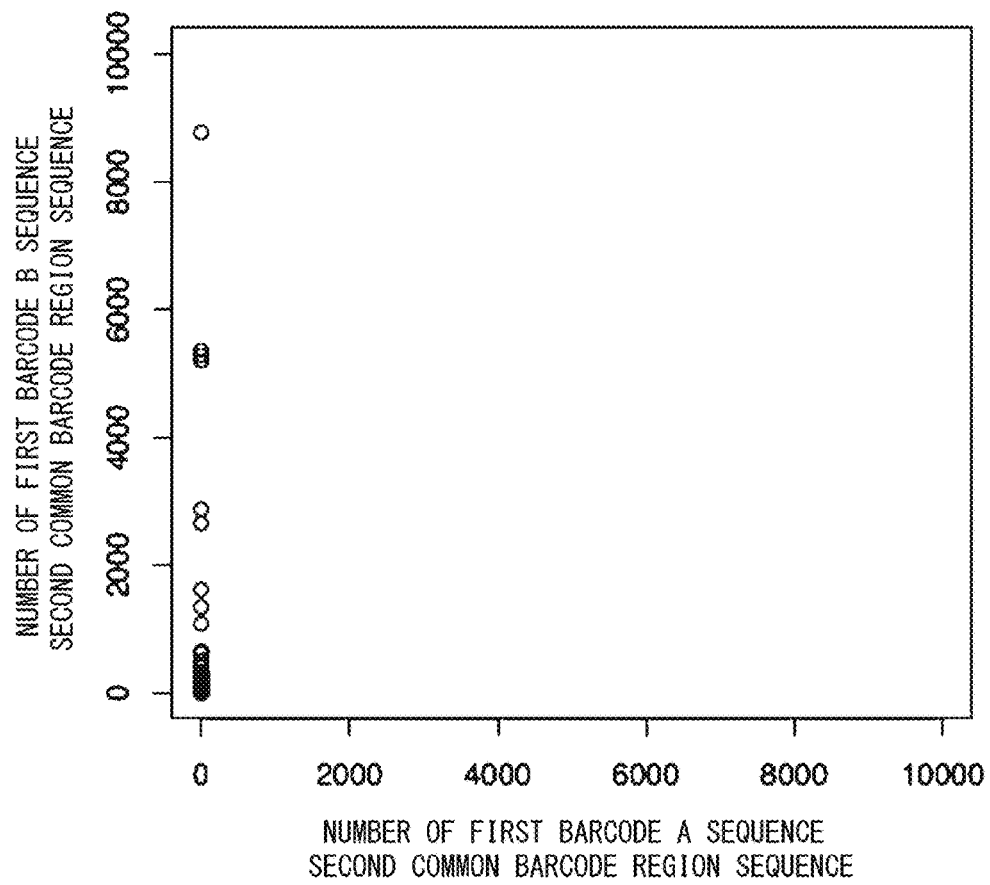
FIG. 15 is a graph (Graph 2) which, for each second unique barcode region sequence of the first barcode sequence side data where the second unique barcode region sequence matched the complementary strand DNA side data, represents the distribution of the count number of the first barcode nucleic acid sequences (two types) detected from the unique reads having the above (negative control cells where the LPS drug was absent) (first barcode nucleic acid sequence A: LPS drug absent, first barcode nucleic acid sequence B: LPS drug present).

The total number of reads of the second common barcode region sequence (16 bases) and the second unique barcode region (12 bases) of the negative control cells without the LPS drug was 185,858. Furthermore, the number of first barcode nucleic acid sequences which can be associated with the second common barcode region sequence (16 bases) and the second unique barcode region (12 bases) was 184,181. Among the above, the ratio of number of reads of the first barcode nucleic acid A corresponding to the presence of the drug LPS to the total number of reads of first barcode nucleic acid was 0% of, and the ratio of number of reads of the first barcode nucleic acid B corresponding to the absence of the drug to the total number of reads of first barcode nucleic acid was 83.3%. Furthermore, after read error correction was carried out, upper list was shown in which the second unique barcode regions having a large number of total number of reads of the second common barcode region sequences which consistent with the first barcode nucleic acid sequence A and the first barcode nucleic acid sequence B, respectively, are arranged in order (Table 2-1 in FIG. 14A and Table 2-2 in FIG. 14B). In addition, among the 197 second unique barcode region sequences of the complementary strand DNAs, 172 sequences identical to the second unique barcode region sequences were found in the first barcode sequence library, and virtually all (>99%) of the first barcode nucleic acid sequences were attributed to the first barcode nucleic acid B (FIG. 15, Graph 2).

Example 7: A Cellular Phenotype Screening Method in Compartments (Droplets)

For cellular phenotype screening of a test substance in which a cell, a test substance, and a first barcode nucleic acid corresponding to the test substance are encompassed and brought into contact in a compartment (droplet), it is possible to use the following method, for example.

7-1

Figure 16:
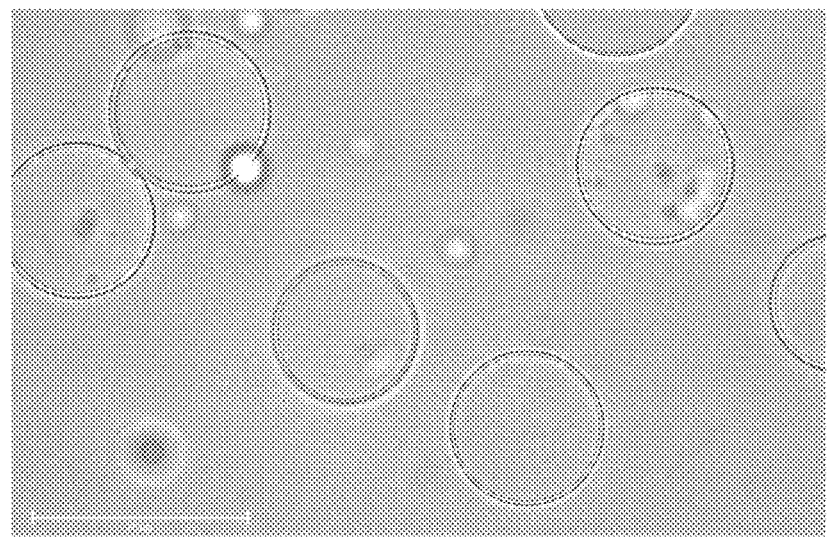
FIG. 16 is a micrograph showing an example of a generated first sub-compartment. (Here, in the example in the photograph, the first sub-compartment was generated without adding the test substance and the first barcode nucleic acid.)

It is possible to generate the first sub-compartment encompassing the test substance and the first barcode nucleic acid corresponding to the test substance according to the following procedure as described in Anal. Chem. 2018, 90, 16, 9813-9820. Specifically, an Opti-MEM medium in which FBS is not included is used and the test substance is dissolved in the aqueous phase. Next, in a well or tube, the aqueous phase, hydrogel particles (for example, gel beads of agarose 1.1 wt % concentration with a size of approximately 70 μm in diameter) generated in advance using a microfluidic device or the like, the first barcode nucleic acid corresponding to the test substance, anchor CMO, and co-anchor CMO are mixed. Next, it is possible to obtain droplets including the test substance and the first barcode nucleic acid corresponding to the test substance as first sub-compartments by adding an organic solvent and a surfactant (for example, Triton-100) to the wells and carrying out a stirring and shaking treatment by a vortex mixer. The micrograph in FIG. 16 is a micrograph of the first sub-compartment generated without adding the test substance and the first barcode nucleic acid. However, droplets with a size of approximately 70 μm in diameter can be generated similarly in the case where the test substance and the first barcode nucleic acid corresponding to the test substance are included in the droplets. Through this treatment, the test substance is associated with the first barcode nucleic acid in the first sub-compartment.

For example, as the organic solvent here, Droplet Generator oil for EvaGreen (manufactured by BioRad Laboratories, Inc.) can be used. Droplet Generator oil for EvaGreen is oxygen permeable and is suitable for intra-droplet culturing of cells. Actually, as a result, the survival rate of cells (THP1 cells) was 88% when the cells were cultured for 24 hours in the droplets generated by this organic solvent and the Opti-MEM medium not including FBS.

7-2

Next, cells (THP1 cells) suspended in the Opti-MEM medium not including FBS are prepared. The cell suspension is poured into the microfluidic device along with the organic solvent and second sub-compartments including the cells are generated during passing through the microfluidic device. The flow rates of the cell suspension and the organic solvent are controlled and the size of the second sub-compartments including the cells is adjusted to approximately 100 μm. Furthermore, the first sub-compartment and second sub-compartment are merged in the microfluidic device by applying a voltage of 350V-500V to generate droplets (compartments) that simultaneously encompass the test substance, a cell, and the first barcode nucleic acid. That is, in the microfluidic device, a group of droplets including the test substance and the first barcode nucleic acid corresponding to the test substance (first sub-compartments) is poured from one channel, and a cell suspension is poured from the other channel, each together with an organic solvent, thereby ultimately generating droplets (compartments) that simultaneously encompass the test substance, a cell, and the first barcode nucleic acid. For example, for the generation of droplets, it is possible to use a flow focusing device according to the description in E. Z. Macosko et al., Highly Parallel Genome-wide Expression Profiling of Individual Cells Using Nanoliter Droplets, Cell. 161, 1202-1214 (2015).

Figure 17:
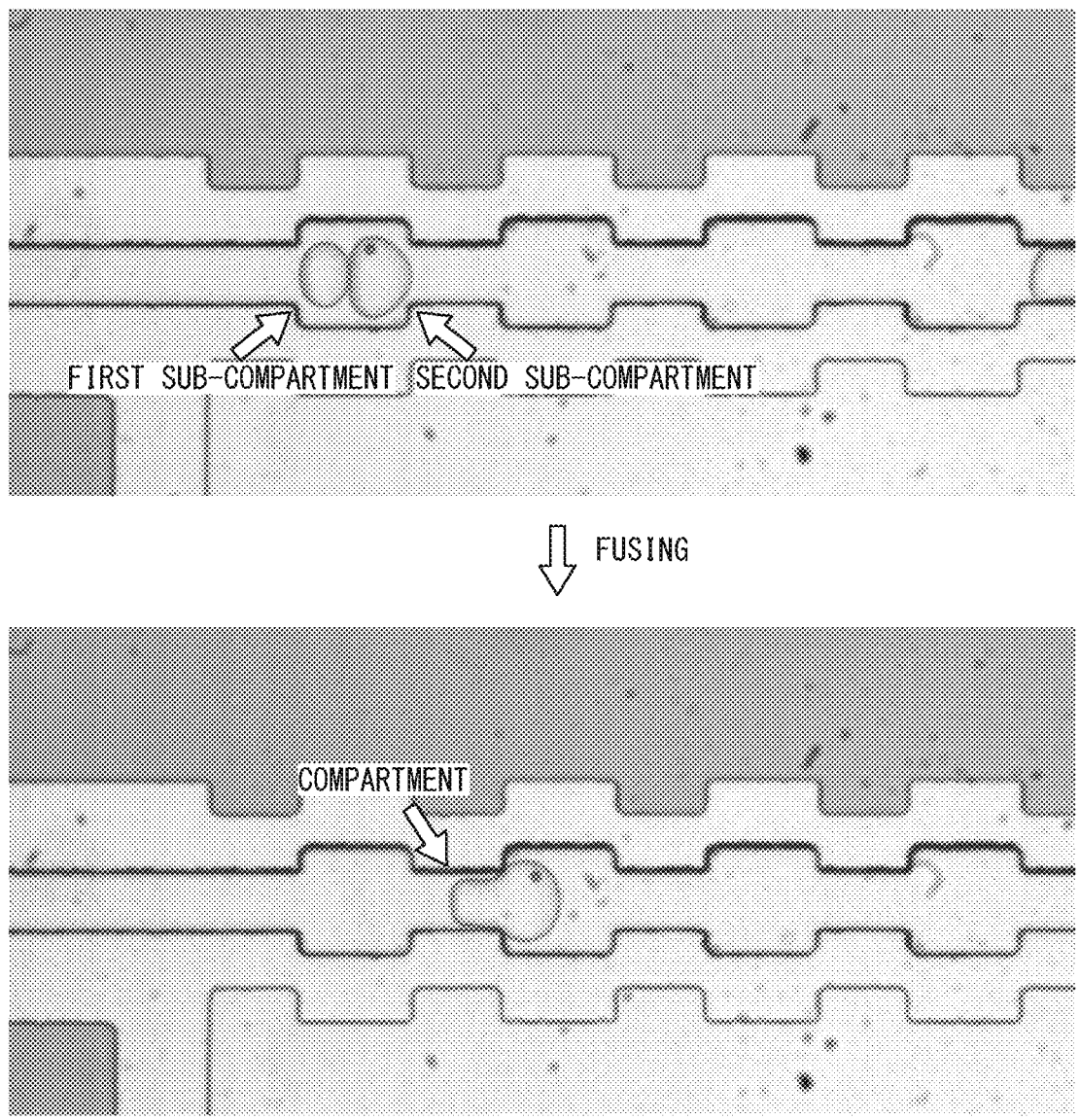
FIG. 17 is micrographs showing a state where a homogeneous droplet (compartment) (approximately 110 μm in diameter) is generated by one-on-one droplet fusion in a microfluidic device.

On the other hand, it is also possible to generate droplets (compartments) by generating the first sub-compartments in advance using a microfluidic device, instead of making them using a stirring and shaking treatment by a vortex mixer with gel beads, and then merging the first sub-compartment with a second sub-compartment including a cell. More specifically, according to the method described in Anal. Chem. 2018, 90, 2, 1273-1279, in a microfluidic device, a group of droplets (first sub-compartments) including the test substance and the first barcode nucleic acid corresponding to the test substance is poured from one channel, and a cell suspension is poured from the other channel, each together with an organic solvent, thereby making it possible to generate droplets (compartments) simultaneously encompassing the test substance, a cell, and the first barcode nucleic acid. For example, as a result of sequentially carrying out one-on-one droplet fusion between a group of droplets including the first barcode nucleic acid (first sub-compartments, size of approximately 70 μm in diameter) and the second sub-compartments including a cell (size of approximately 100 μm in diameter) in the microfluidic device, it was confirmed that homogeneous droplets (compartments) (diameter of approximately 110 μm) were generated stably, as shown in the micrograph in FIG. 17.

7-3

In the droplets (compartments) in the organic solvent phase described above, while the cells are affected by the test substance, it makes possible to attach the first barcode nucleic acid corresponding to the test substance to the cell surface and to tag the cells with the first barcode nucleic acid concurrently.

7-4

Next, it is possible to recover the cells from the compartments (droplets) by the following process. Using a microchip or the like, 100 μL of the droplets (compartments including cells which are affected by the test substance and tagged with the first barcode nucleic acid) is collected and transferred to a microtube containing 500 μL of a fluorine solvent (for example, hydrofluoroether (HFE), Novec (trademark) 7200 High Performance Liquid (manufacture by 3M Japan)) in a lower layer. To disrupt the droplets, 300 μL of another organic solvent (for example, perfluoro-n-octanol) is added to this mixture, and the microtubes are shaken vigorously for 10 seconds and then left to stand. Consequently, the mixture is separated into two layers of an aqueous phase including cells tagged with the first barcode nucleic acid and an organic solvent phase, and it is possible to recover cells tagged with the first barcode nucleic acid from the aqueous phase and to prepare a cell mixture solution.

When recovering the cells from the compartments (droplets), in addition to a method using organic solvents, it is also possible to disrupt the droplets using an anti-static gun (for example, Zerostat 3). Using a microchip or the like, 100 μL of the droplets (compartments including cells which are affected by the test substance and tagged with the first barcode nucleic acid A) is collected and transferred to a microtube containing 100 μL of a fluorine solvent (for example, hydrofluoroether (HFE), Novec (trademark) 7200 High Performance Liquid (manufactured by 3M Japan)) in a lower layer. It is possible to disrupt the droplets by pulling back the trigger of the anti-static gun approximately 10 times to this microtube. The cells tagged with the first barcode nucleic acid A are recovered from the aqueous phase to prepare the cell mixture solution. The method to disrupt the droplets using an anti-static gun can be performed according to the method described in Biomicrofluidics. 22(4):044107, 2017, for example.

7-5

Next, using an imaging cell sorter, cells are sorted and recovered from the cell mixture solution based on the cellular image phenotype observed in response to the addition of the test substance (for example, nuclear localization of proteins in response to stimulation or drug treatment). Specifically, the method for sorting cells in which changes in the cellular image phenotype occurred in response to the test substance by an imaging cell sorter is able to be performed by the same method as in Example 4, for example.

7-6

Next, in the same manner as Example 6, single cell analysis is performed on the cell mixture solution sorted and recovered by the imaging cell sorter, and information of the test substance is associated with information of cellular phenotype of the cells sorted and recovered by the imaging cell sorter. When reading out the DNA barcode modifying each cell and cell-derived genetic information, it is possible to use the Chromium Controller apparatus and the Single Cell 3' Reagent Kit v3 manufactured by 10× Genomics, which is a single cell analysis technology using a droplet technique as in Example 5. In addition, it is also possible to use the same reagent kit for reading out of the gene expression information of the recovered cells.

Example 8: Cellular Phenotype Screening Method Using 96-Well Microplate

Figure 18:
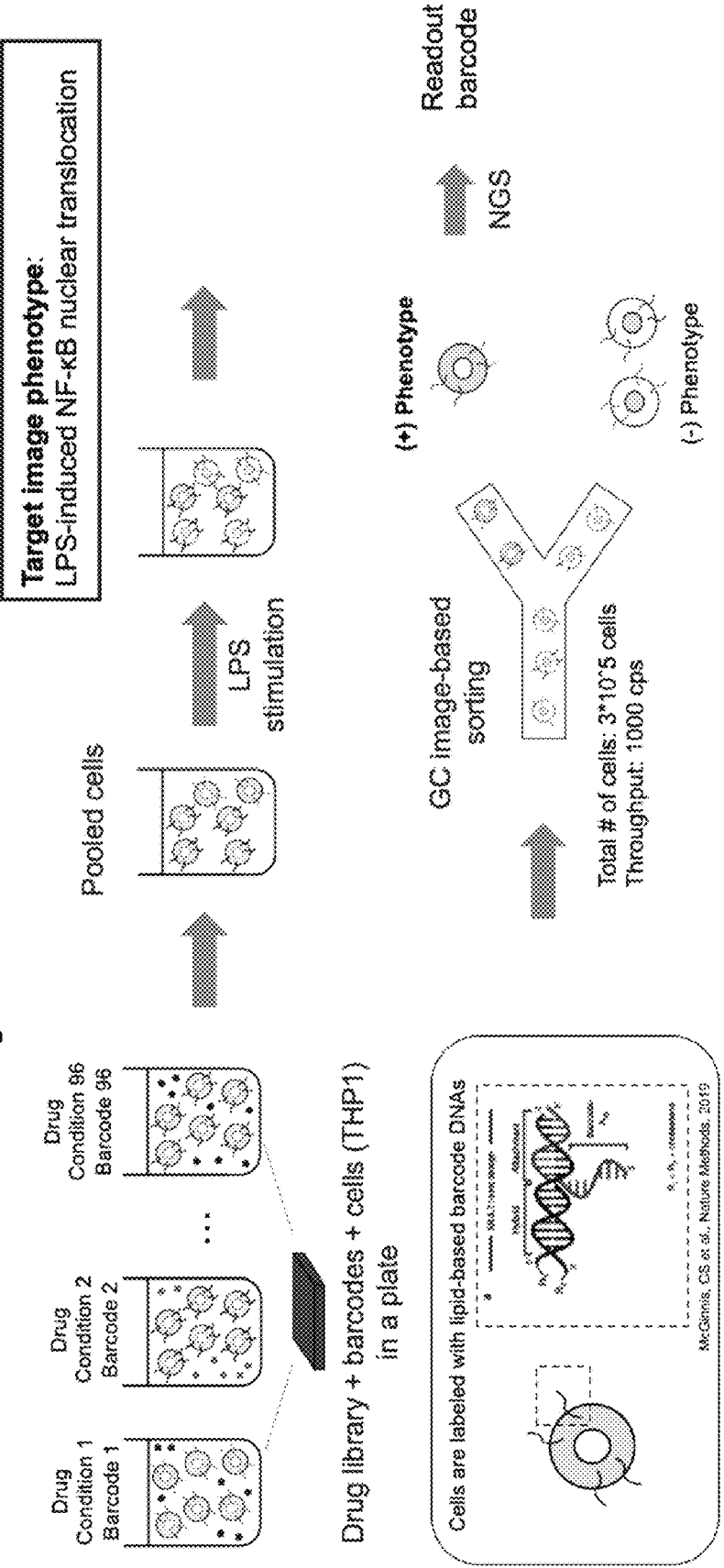
FIG. 18 is a schematic diagram of the cellular phenotype screening method of Example 8 using a 96-well microplate in order to search for test targets which cause a desired phenotypic change.

In accordance with the schematic diagram illustrated in FIG. 18, a search was carried out for test targets which cause a desired phenotypic change (in the example of FIG. 18, test substances which inhibit nuclear localization of NF-κB induced by LPS).

Specifically, in each well of a 96-well microplate, the first barcode nucleic acids were attached to cells (THP1 cells) according to the method described in Reference Example 1 and further brought into contact with test substances. At this time, different types and concentrations of the test substance and different types of the first barcode nucleic acids were used in each well. Due to this, 96 types of test targets (24 types of test substances ×4 types of concentrations) were associated with 96 types of first barcode nucleic acids which are attached to the cells (THP1 cells).

The 96 types of test targets (24 types of test substances × 4 types of concentrations) and the functions (known mechanisms of action) of the test substances used in this experiment were as shown in FIG. 19. In addition, the sequences of the first barcode nucleic acid (Barcode #) used in this experiment were as shown in FIGS. 20A to 20C. The sequence of each first barcode nucleic acids used was different for each test target individually, and the first barcode nucleic acid was associated with the test targets.

In this test, a test was carried out by a method for bringing each test substance, the first barcode nucleic acid corresponding to the test substance, and the cells into contact in each well of a 96-well microplate.

Next, using an imaging cell sorter, cells were sorted and recovered from the cell mixture solution based on the cellular image phenotype (presence or absence of nuclear localization of NF-κB protein in response to LPS stimulation) observed in response to the addition of the test substances.

Next, in the same manner as the examples described above, a single cell analysis was performed on the cell mixture solution sorted and recovered by the imaging cell sorter. Specifically, when reading out the DNA barcodes modifying each cell and cell-derived genetic information, the Chromium Controller apparatus and the Single Cell 3' Reagent Kit v3 manufactured by 10× Genomics, which is a single cell analysis technology using a droplet technique as in Example 5 and Example 6, were used.

Figure 21:
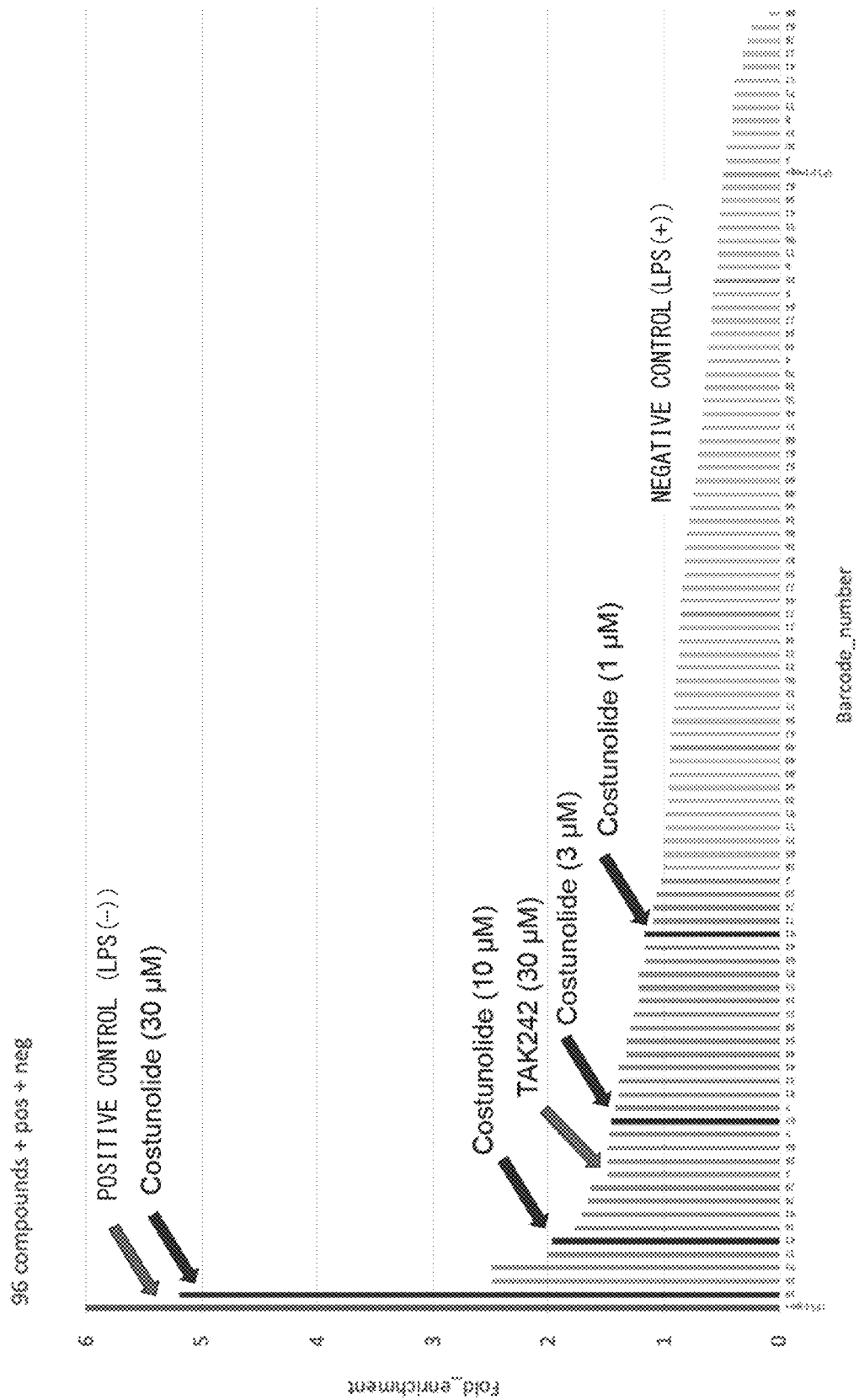
FIG. 21 is a graph showing the enrichment levels of the first barcode nucleic acid sequences of the sorted cells in Example 8.

The enrichment levels of the first barcode nucleic acid sequence of the sorted cells were as shown in FIG. 21. Here, the value on the vertical axis exceeds 1 means that the sample is more concentrated than the sample before sorting.

The positive control (LPS (−): nuclear localization of NF-κB does not occur) was enriched approximately 20-fold by image sorting.

The cell group using a known NF-κB nuclear localization inhibitor (TAK242: 30 μM) as the test substance was enriched approximately 1.5-fold by image sorting.

In addition, among the randomly added test substances, the cell group using Costunolide as the test substance was significantly enriched (Constunolide: anti-inflammatory activity).

Additionally, there were few negative-control (LPS (+): nuclear localization of NF-κB occurs) included in the sorted sample.

Figure 22:
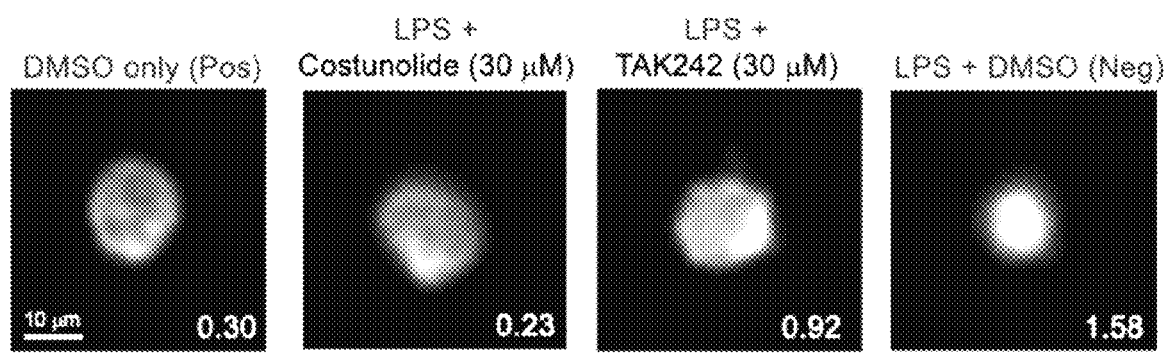
FIG. 22 is photographs in which whether or not the cells sorted and recovered by the imaging cell sorter in Example 8 certainly exhibit the phenotype was confirmed by capturing photographic images of the cells and calculating the nuclear localization score using an existing image flow cytometer.

FIG. 22 is photographs in which whether or not the cells sorted and recovered by the imaging cell sorter certainly exhibit the phenotype was confirmed. The photographic images of the cells were captured by an image flow cytometry and the nuclear localization scores were also calculated by the imaging flow cytometry. Regarding the nuclear localization scores, a higher value indicates a higher degree of nuclear localization. A is a cell corresponding to positive control (LPS (−): nuclear localization of NF-κB does not occur), B is a cell treated with LPS and a known NF-κB nuclear localization inhibitor (TAK242: 30 μM) as a test substance, C is a cell treated with LPS and Costunolide, which is a test substance selected as a candidate by the cellular phenotype screening, and D is a cell corresponding to negative control (LPS (+): nuclear localization of NF-κB occurs). The nuclear localization scores of a cell corresponding to the positive control (LPS (−): nuclear localization of NF-κB does not occur), a cell treated with LPS and a known NF-κB nuclear localization inhibitor (TAK242: 30 μM) as a test substance, a cell treated with LPS and Costunolide which is a test substance selected as a candidate by the cellular phenotype screening, and cell D corresponding to a negative control (LPS (+): nuclear localization of NF-κB occurs) were found to be 1.58, 0.92, 0.23, and 0.30, respectively.

As described above, according to the present disclosure, using the imaging cell sorter, it is possible to perform a cellular phenotype screening of test targets by sorting a cell to which a nucleic acid barcode corresponding to each of the test targets was attached based on the cellular image phenotype observed according to the test target, reading the attached barcode nucleic acid sequence, and further reading the genes of each cell.

REFERENCE SIGNS LIST

1: Light source
3: Light-irradiated region
5: Observation object
7: Light receiving unit
9: Storage unit
11: Analysis unit
13: Optical system control unit
25: Light receiving region
27: Light receiving system control unit

What is claimed is:

1. A method for screening a test target, the method comprising:
    a step of preparing a plurality of cells which are tagged with a first barcode nucleic acid associated with a test target and treated with the test target;
    a step of sorting the plurality of cells based on cellular phenotype using an imaging cell sorter; and
    a step of identifying the test target used to treat each cell using the first barcode nucleic acid as an indicator.

2. The method according to claim 1, wherein the test target used to treat each cell is associated with a phenotype of each cell.

3. The method according to claim 1, further comprising: a step of analyzing genome-related information of each cell.

4. The method according to claim 1, wherein the step of preparing cells includes a step of associating the first barcode nucleic acid with the cells by mixing a liquid medium including the test target and the first barcode nucleic acid with the cell.

5. The method according to claim 1, wherein the step of preparing cells includes a step of associating the first barcode nucleic acid with the test target by adding hydrogel beads to a liquid medium including the test target and the first barcode nucleic acid to generate a first sub-compartment including the test target and the first barcode nucleic acid.

6. The method according to claim 1, wherein the step of preparing cells includes fusing a first sub-compartment including the test target and the first barcode nucleic acid and a second sub-compartment including the cell to generate a compartment including the test target, the first barcode nucleic acid, and the cell.

7. The method according to claim 6, wherein the step of preparing cells includes treating the cells with the test target in the compartment.

8. The method according to claim 6, wherein the compartment or sub-compartment is a droplet.

9. The method according to claim 6, wherein the step of preparing cells includes a step of recovering the cells from the compartment.

10. The method according to claim 1, wherein the sorting step includes a step of sorting cells in which a predetermined reaction occurs due to the test target, based on cellular phenotype.

11. The method according to claim 3, wherein the step of analyzing genome-related information includes
    a step of preparing a plurality of compartments including a genome-related nucleic acid corresponding to a cell genome or a derivative thereof, the first barcode nucleic acid, and a second barcode nucleic acid linking bead, in which the second barcode nucleic acid linking bead includes a plurality of second barcode nucleic acids hybridizable with the cell genome or the genome-related nucleic acid corresponding to a derivative thereof or the first barcode nucleic acid,
    a step of obtaining a hybridized complex by hybridizing each of the genome-related nucleic acid and the first barcode nucleic acid, with the second barcode nucleic acid,
    a step of producing an amplified product derived from the hybridized complex, and
    a step of detecting genome-related information of the cell after its coexistence with the test target using an expression pattern of the amplified product as an indicator.

12. The method according to claim 11, wherein the genome-related nucleic acid is cell genome DNA, or RNA derived from the cell genome or cDNA thereof.

13. The method according to claim 11, wherein each first barcode nucleic acids includes a first common barcode region which is common to the same test target and a first hybridization region hybridizable with the second barcode nucleic acid.

14. The method according to claim 11, wherein sequence information of the first common barcode region is an indicator for specifying the test target.

15. The method according to claim 11, wherein each of the plurality of second barcode nucleic acids linked to the second barcode nucleic acid linking bead includes a second common barcode region which is common to each other, a second unique barcode region able to be distinguished from each other, and a second hybridization region hybridizable with the genome-related nucleic acid or the first barcode nucleic acid.

16. The method according to claim 11,
wherein sequence information of the second unique barcode region is an indicator for specifying the genome-related nucleic acid.

17. The method according to claim 11,
wherein the second hybridization region includes a nucleic acid complementary to the first hybridization region or the genome-related nucleic acid.

18. The method according to claim 1,
wherein the imaging cell sorter is an analysis apparatus provided with an optical modulation unit having a plurality of regions with different optical characteristics from each other is arranged on an optical path between the light source and the light-irradiated region, an analysis unit in which scattered light, transmitted light, fluorescent light, or electromagnetic waves from an observation object present in a light-irradiated region irradiated with light from a light source are received and converted to electrical signals by a light receiving unit and the observation object is analyzed based on signals extracted in time sequence from the electrical signals which are output from the light receiving unit, and a sorting unit which classifies the observation object and sorts the observation object based on analysis results of the analysis unit.

19. The method according to claim 18,
wherein the analysis unit updates a classification algorithm based on analysis results.

20. The method according to claim 1,
wherein the test target includes a test substance.

* * * * *

SEQUENCE LISTING

<160> NUMBER OF SEQ ID NOS: 8

<210> SEQ ID NO 1
<211> LENGTH: 41
<212> TYPE: DNA
<213> ORGANISM: Artificial Sequence
<220> FEATURE:
<223> OTHER INFORMATION: Nucleic acids in Linker

<400> SEQUENCE: 1
gtaacgatgg agctgtcact tggaattctc gggtgccaag g         41

<210> SEQ ID NO 2
<211> LENGTH: 20
<212> TYPE: DNA
<213> ORGANISM: Artificial Sequence
<220> FEATURE:
<223> OTHER INFORMATION: Nucleic acids in Linker

<400> SEQUENCE: 2
agtgacagct ggatcgttac         20

<210> SEQ ID NO 3
<211> LENGTH: 59
<212> TYPE: DNA
<213> ORGANISM: Artificial Sequence
<220> FEATURE:
<223> OTHER INFORMATION: First barcode nucleic acids A

<400> SEQUENCE: 3
ccttggcacc cgagaattcc accacaatga aaaaaaaaa aaaaaaaaaa aaaaaaaa         59

<210> SEQ ID NO 4
<211> LENGTH: 59
<212> TYPE: DNA
<213> ORGANISM: Artificial Sequence
<220> FEATURE:
<223> OTHER INFORMATION: First barcode nucleic acids B

<400> SEQUENCE: 4
ccttggcacc cgagaattcc atgagaccta aaaaaaaaa aaaaaaaaaa aaaaaaaa         59

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
cttggcaccc gagaattcc         19

<210> SEQ ID NO 6
<211> LENGTH: 58
<212> TYPE: DNA
<213> ORGANISM: Artificial Sequence
<220> FEATURE:
<223> OTHER INFORMATION: Primer

<400> SEQUENCE: 6
aatgatacgg cgaccaccga gatctacact ctttccctac acgacgctct tccgatct         58

<210> SEQ ID NO 7
<211> LENGTH: 63
<212> TYPE: DNA
<213> ORGANISM: Artificial Sequence

```
-continued

<220> FEATURE:
<223> OTHER INFORMATION: Primer

<400> SEQUENCE: 7
caagcagaag acggcatacg agatattggc gtgactggag ttccttggca cccgagaatt      60
cca                                                                    63

<210> SEQ ID NO 8
<211> LENGTH: 63
<212> TYPE: DNA
<213> ORGANISM: Artificial Sequence
<220> FEATURE:
<223> OTHER INFORMATION: Primer

<400> SEQUENCE: 8
caagcagaag acggcatacg agattacaag gtgactggag ttccttggca cccgagaatt      60
cca                                                                    63
```